US010444202B2

(12) United States Patent
Flynn et al.

(10) Patent No.: US 10,444,202 B2
(45) Date of Patent: Oct. 15, 2019

(54) NONDESTRUCTIVE INSPECTION USING CONTINUOUS ULTRASONIC WAVE GENERATION

(71) Applicant: Los Alamos National Security, LLC, Los Alamos, NM (US)

(72) Inventors: Eric B. Flynn, Santa Fe, NM (US); Charles R. Farrar, Los Alamos, NM (US); Gregory James Sylvester Jarmer, Albuquerque, NM (US)

(73) Assignee: Triad National Security, LLC, Los Alamos, NM (US)

( * ) Notice: Subject to any disclaimer, the term of this patent is extended or adjusted under 35 U.S.C. 154(b) by 663 days.

(21) Appl. No.: 14/688,854

(22) Filed: Apr. 16, 2015

(65) Prior Publication Data
US 2015/0300995 A1 Oct. 22, 2015

Related U.S. Application Data

(60) Provisional application No. 61/980,488, filed on Apr. 16, 2014.

(51) Int. Cl.
G01N 29/46 (2006.01)
G01N 29/24 (2006.01)
(Continued)

(52) U.S. Cl.
CPC ............ *G01N 29/46* (2013.01); *G01N 29/12* (2013.01); *G01N 29/2418* (2013.01);
(Continued)

(58) Field of Classification Search
CPC .... G01N 29/46; G01N 29/12; G01N 29/2418; G01N 29/2437
See application file for complete search history.

(56) References Cited

U.S. PATENT DOCUMENTS 3,772,457 A 11/1973 Macovski
4,539,847 A 9/1985 Paap
(Continued)

FOREIGN PATENT DOCUMENTS

CA 2 516 197 1/2013

OTHER PUBLICATIONS

Castellini et al., "Laser Doppler Vibrometry for Structural Dynamic Characterization of Rotating Machinery," *Applied Mechanics and Materials*, vol. 415, Sep. 2013, pp. 538-543.
(Continued)

*Primary Examiner* — Seahvosh Nikmanesh
(74) *Attorney, Agent, or Firm* — Klarquist Sparkman, LLP

(57) ABSTRACT

Methods and apparatus are disclosed for analyzing structures by applying a continuous ultrasonic excitation and measuring steady state response of the structures using laser Doppler vibrometery, or other techniques. In one example, a method comprises applying a continuous signal having one or more periodic tones to the structure, generating measurements of wave response to the signal at each of a plurality of inspection points of the structure, and, for each of the periodic tones, estimating wavenumbers for a number of the inspection points of the structure based on the wave response measurements and the frequency of the periodic tones. The estimated wavenumbers can be used to determine properties of the structure, including defects, damage, or variation in thickness.

24 Claims, 18 Drawing Sheets

(51) Int. Cl.
  *G01N 29/12* (2006.01)
  *G01N 29/265* (2006.01)
(52) U.S. Cl.
  CPC ....... *G01N 29/2437* (2013.01); *G01N 29/265* (2013.01); *G01N 2291/02818* (2013.01); *G01N 2291/02827* (2013.01); *G01N 2291/02854* (2013.01); *G01N 2291/02881* (2013.01)

(56) References Cited

U.S. PATENT DOCUMENTS

| | | | |
|---|---|---|---|
| 4,824,250 | A | 4/1989 | Newman |
| 5,062,296 | A | 11/1991 | Migliori |
| 5,956,143 | A | 9/1999 | Kotidis |
| 6,078,397 | A | 6/2000 | Monchalin et al. |
| 6,532,821 | B2 | 3/2003 | Lamouche et al. |
| 6,837,109 | B2 | 1/2005 | Okuno et al. |
| 7,079,258 | B2 | 7/2006 | Selbach et al. |
| 7,116,428 | B2 | 10/2006 | Sauerland et al. |
| 7,278,315 | B1 | 10/2007 | Klein et al. |
| 7,649,632 | B2 | 1/2010 | Murray |
| 7,876,453 | B1 | 1/2011 | Williams et al. |
| 7,965,394 | B2 | 6/2011 | Chen et al. |
| 8,004,689 | B2 | 8/2011 | Monchalin et al. |
| 8,248,595 | B2 | 8/2012 | Ochiai et al. |
| 8,322,221 | B1 | 12/2012 | Sathish et al. |
| 8,497,986 | B2 | 7/2013 | Ochiai et al. |
| 8,531,915 | B2 | 9/2013 | Ammar |
| 2010/0312493 | A1* | 12/2010 | Purekar ............ G01N 17/02 702/35 |

OTHER PUBLICATIONS

Flynn et al., "Structural imaging through local wavenumber estimation of guided waves," *NDT&E International*, vol. 59, Oct. 2013, pp. 1-10.

Flynn et al., "High-Speed, Non-Contact, Baseline-Free Imaging of Hidden Defects Using Scanning Laser Measurements of Steady-State Ultrasonic Vibration," *Structural Health Monitoring 2013: A Roadmap to Intelligent Structures: Proceedings of the Ninth Int'l Workshop on Structural Health Monitoring*, Sep. 10, 2013, pp. 1186-1193.

Gasparoni et al., "Experimental Modal Analysis on a Rotating Fan Using Tracking-CSLDV," 14 pages (also published as "Experimental Modal Analysis on a Rotating Fan Using Tracking-CSLDV," *AIP Conference Proceedings*, vol. 1253, No. 1, Jun. 2010, pp. 3-16).

Lee et al., "Repeat scanning technology for laser ultrasonic propagation imaging," *Measurement Science and Technology*, vol. 24, No. 8, Jun. 20, 2013, 11 pages.

Martarelli et al., "Performance analysis of continuous tracking laser Doppler vibrometery applied to rotating structures in coast-down," *Meas. Sci. Tech.* vol. 23, No. 6, Apr. 30, 2012, 13 pages.

Martarelli et al., "Characterization of Rotating Structures in Coast-down by means of Continuous Tracking Laser Doppler Vibrometer," 8 pages (also published as Martarelli et al., "Characterization of Rotating Structures in Coast-down by means of Continuous Tracking Laser Doppler Vibrometer," *Modal Analysis Topics*, vol. 3, 2011, pp. 525-532).

Mechri et al., "Depth-profiling of elastic inhomogeneities in transparent nanoporous low-k materials by picosecond ultrasonic interferometry," Applied Physics Letters, vol. 95, 2009, pp. 091907-1 through 091907-3.

Michaels et al., "Frequency-wavenumber domain methods for analysis of incident and scattered guided wave fields," *Proc. of SPIE: Health Monitoring of Structural and Biological System 2009*, vol. 7295, 2009, pp. 729513-1 through 729513-12.

Rogge et al., "Characterization of impact damage in composite laminates using guided wavefield imaging and local wavenumber domain analysis," *Ultrasonics*, vol. 53, No. 7, Sep. 2013, pp. 1217-1226.

Ruzzene, "Frequency-wavenumber domain filtering for improved damage visualization," *Smart Mater. Struct.*, vol. 16, Oct. 8, 2007 pp. 2116-2129.

Ruzzene, "Frequency-Wavenumber Domain Filtering for Damage Visualization," *QNDE 2006: Review of Progress in Quantitative Nondestructive Evaluation*, Portland, Ore. Aug. 3, 2006, 32 pages.

Salman et al., "Surface wave measurements using a single continuously scanning laser Doppler vibrometer: application to elastography," *J. Acoust. Soc. Am.*, Mar. 2013, vol. 133, No. 3, pp. 1245-1254.

Sinha et al., "Acoustic Sensor for Pipeling Monitoring: Technology Report," *Los Alamos Nat'l Lab. Report No. LA-UR-05-6025*, document marked Jul. 20, 2005, 23 pages.

* cited by examiner

FIG. 4
400
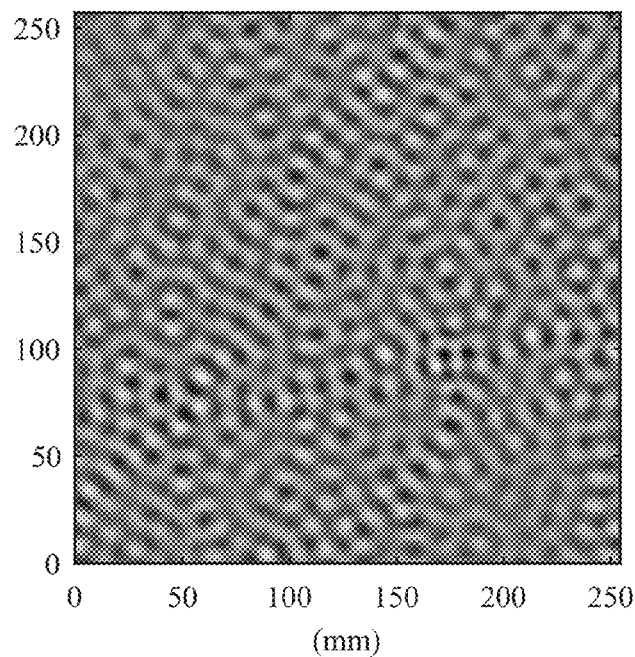
410
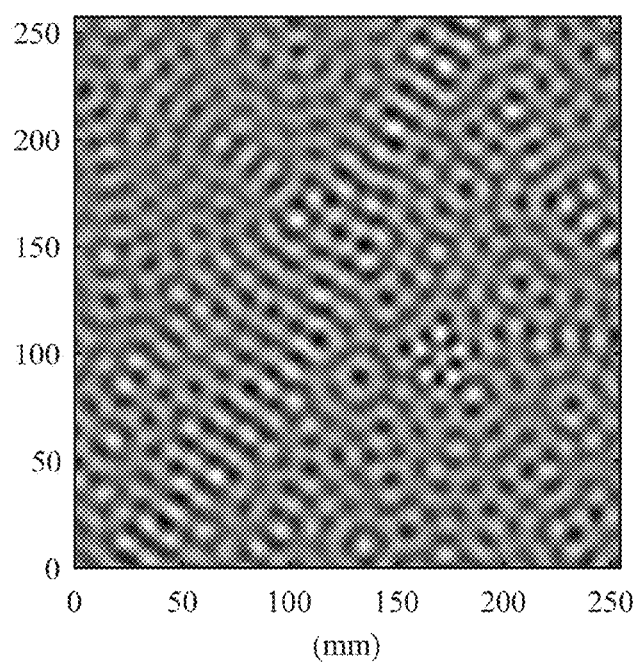

$$c[x, y] = \hat{a}[x, y] + j\hat{b}[x, y]$$

FIG. 7E
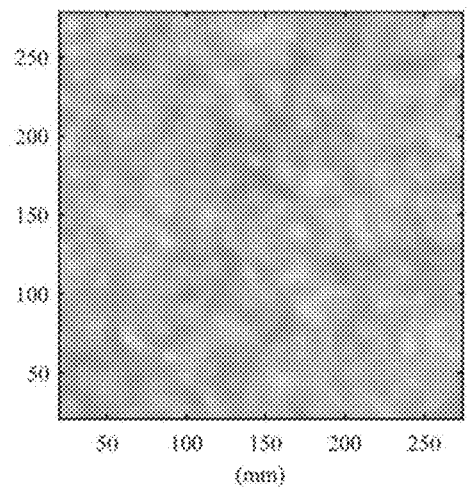
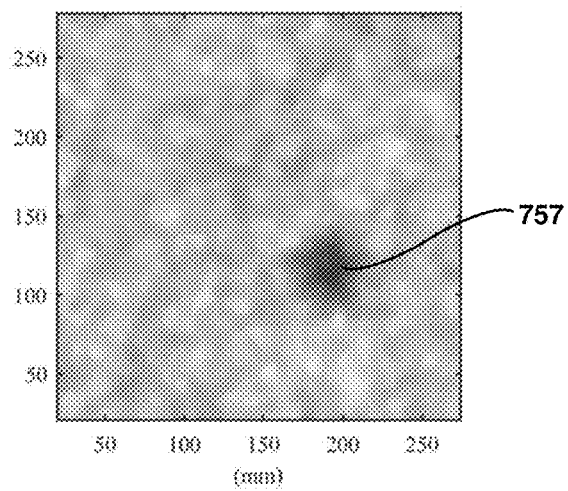
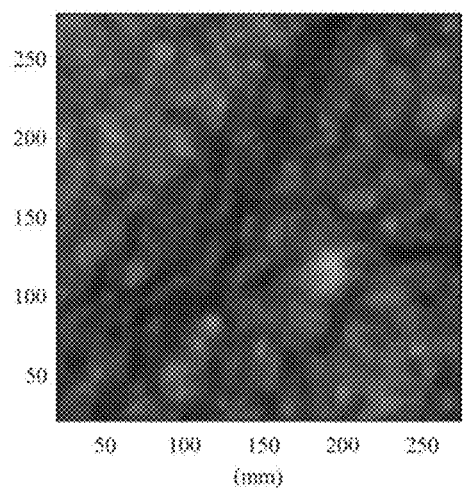

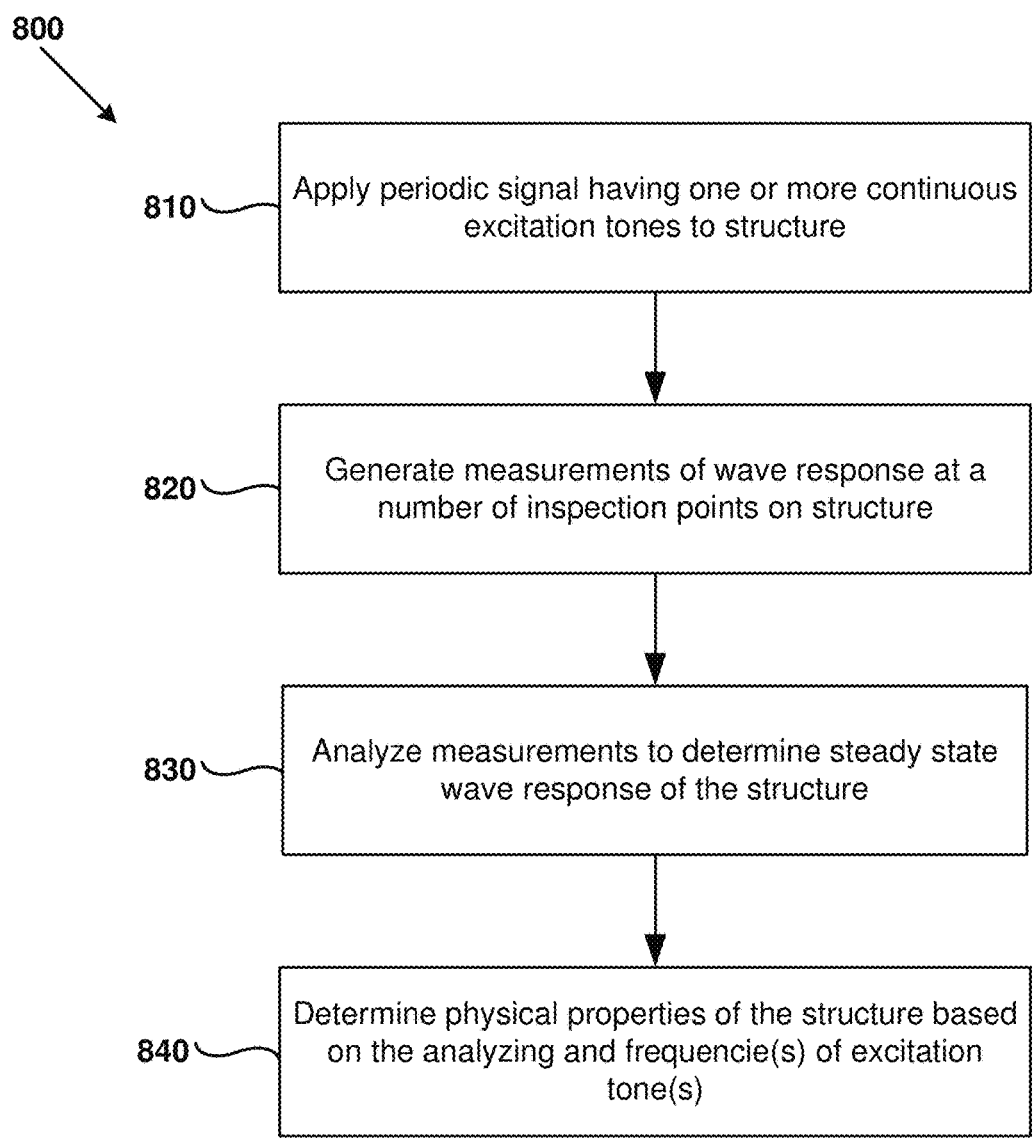

NONDESTRUCTIVE INSPECTION USING CONTINUOUS ULTRASONIC WAVE GENERATION

CROSS-REFERENCE TO RELATED APPLICATIONS

This application claims the benefit of U.S. Provisional Application No. 61/980,488, entitled "Method for Nondestructive Inspection Using Continuous Ultrasonic Wave Generation," filed Apr. 16, 2014, the disclosure of which is incorporated herein by reference in its entirety.

ACKNOWLEDGMENT OF GOVERNMENT SUPPORT

This invention was made with government support under Contract No. DE-AC52-06NA25396 awarded by the U.S. Department of Energy. The government has certain rights in the invention.

BACKGROUND

Resonant ultrasound spectroscopy and acoustic interferometry are two techniques that use temporal-frequency information, such as resonant frequencies, as fingerprints for identifying and/or characterizing inspected specimens. Such information is derived from full-body responses of the specimen, so they can provide bulk properties such as elastic moduli or density. They can also use these fingerprints to identify specimens that are dissimilar. However, these techniques are unable to provide local information about specimens, such as where an irregularity is, what type it is, or how large it is.

The most common forms of ultrasonic inspection utilize short-duration ultrasonic pulses for interrogation. A short duration pulse will propagate through the specimen being inspected, speeding up, slowing down, attenuating, reflecting, and scattering, depending on the composite of the specimen. Measurements of the wave after it has passed through the specimen allow one to discern the properties/structure of the specimen.

When making measurements at many inspection points, an inspection system must wait for each previous excitation pulse to sufficiently disperse in the specimen or in the surrounding fluid (air or otherwise) so as to prevent it from significantly affecting subsequent measurements. Excitation and sensing may be provided by using roving vibration transducers on or in proximity to the specimen or through optical means such as Q-switched lasers for excitation and laser interferometry or Doppler vibrometry for sensing.

State of the art remote inspection systems utilize a laser for excitation and a laser for sensing. A pulsed laser provides the short-duration excitation through local thermo-elastic expansion on the specimen. The pulse energy is limited to the laser damage threshold of the specimen being inspected. A laser Doppler vibrometer (LDV) then measures the response at each inspection point. Either or both lasers may be scanned over the structure. The low sensitivity of the LDVs in the ultrasonic range often means that multiple measurements must be made at each inspection point and averaged, further reducing the scan rate.

Continuous scanning laser Doppler vibrometry (CSLDV) has been used to rapidly measure the operating deflection shape (ODS) of inspected systems using continuous excitation. The scanning, acquisition, and processing techniques, however, limit systems to relatively low frequencies, which means only global system vibration responses can be measured, providing no local information on specimen properties/structure. Therefore, ample opportunity exists for improvements to measurement technologies.

SUMMARY

Exemplary methods and apparatus disclosed herein include extraction of local wave propagation properties using steady, periodic ultrasonic excitation and continuous-scan sensing or direct imaging to enable non-invasive, high-rate, high-resolution, ultrasonic imaging. In some examples of the disclosed technology, spatial-frequency (e.g., wavenumber) information is utilized for "fingerprinting," instead of temporal-frequency. Since wavenumber is a local phenomenon (unlike resonance), the spatial frequency information gathered is also local, allowing the generation of, for example, maps of local properties and/or structure of a specimen under test.

In some examples of the disclosed technology, excitation of a specimen uses a signal that is constructed from one or more single frequency tones. In some examples, the signal does not pause, even between inspection points. The applied steady-state excitation causes the specimen to reach a steady vibration response state, where the vibration at each point in the structure is similarly composed of one or more tones. The steady excitation may be provided, for example by a temporarily affixed transducer, a permanently installed transducer, a vibrating platform or fixture, or a repeating Q-switched laser. Estimates of specimen properties/structure are made by measuring the shape of the steady-state response across spatially distributed inspection points.

A scanning system, such as a scanning laser Doppler vibrometer (LDV) or an interferometer with a CCD camera can be used to measure response of the specimen. Using scanning laser Doppler vibrometer (LDV) technology allows the measurement of full-field time histories of propagating ultrasonic waves in a structure. Using steady-state waves allows larger amounts of energy to be effectively "pumped" into the structure under test than with transient wave approaches, resulting in much higher (e.g., orders of magnitude) higher displacement of the sample. Further, steady-state waves can allow for avoiding delay between measurements as transient waves dissipate. And typically, fewer cycles of the excited wave are sufficient to effectively capture wave behavior at the inspection points. Thus, technologies disclosed herein can allow the ability to extract time-invariant wave properties that can be used to infer properties of the specimen under test.

In some examples of the disclosed technology, steady-state waves are induced in a specimen under test, and, by extracting time-invariant properties of the waves, damage, defects, or other variations in the specimen can be detected. In some examples of the disclosed technology, a method includes estimating local wavenumber using steady-state response measurements. Wavenumber, the inverse of wavelength, is the spatial analogy of frequency and is fixed for a given frequency, wave-mode, thickness, and set of material properties. When the specimen under test is an anisotropic plate, wavenumber is also a function of propagation direction. As such, changes in wavenumber can be a clear indicator of damage, defects, or other variations, each of which often alter the material geometry or effective properties, at or near the location exhibiting wavenumber changes.

In some examples of the disclosed technology, a method for analyzing a structure comprises applying a continuous signal having one or more periodic tones to the structure, generating measurements of wave response to the signal at each of a plurality of inspection points of the structure, and for each of the periodic tones, estimating a wavenumber for a number of the inspection points of the structure based on the wave response measurements.

In some examples, the continuous signal is applied by using a piezoelectric transducer in physical communication with the structure, while in other examples, the continuous signal is applied by projecting a laser light onto a surface of the structure. In some examples, the periodic tones have frequencies substantially in a range of 30-500 kHz. In some examples, the measurements are generated using a laser Doppler vibrometer. In some examples, the method further comprises composing the wavenumber into a map of properties of the structure, the mapped properties including at least one or more of the following: thickness, density, material composition, elasticity, or temperature.

In other examples of the disclosed technology, a method of analyzing measurement data generated by measuring vibration produced in a structure when applying a continuous signal having one or more excitation tones includes analyzing the measurement data to determine a steady state wave response of the structure, and based on the analyzing and the respective frequency of at least one of the excitation tones, determining one or more physical properties of the structure.

In some examples of the method, the measurement data is time domain data, and the analyzing comprises transforming at least a portion of the measurement data into spatial frequency domain data. In some examples, the transforming is performed by calculating a time-domain discrete Fourier transform of the measurement data, for example, using a Fast Fourier Transform. In other examples, the transforming is performed by calculating a complex response matrix based on mapping phase-synchronized values to a grid of spatial sampling points.

In some examples of the method, analyzing includes mapping the vibratory data to a two-dimensional matrix of complex response values, isolating one or more individual guided-wave modes from spatial frequency domain data, decomposing spatial frequency domain data according to a set of wavenumbers, producing a wavenumber amplitude field by calculating amplitude of decomposed spatial frequency domain data, and/or producing a wavenumber by determining, for a number of inspection points in the measurement data, a wavenumber maxima for an amplitude field within an inspection area used to generate the measurement data.

In some examples, the method further includes generating the measurement data by applying the continuous signal to the structure and generating measurements of wave response to the signal at each of a plurality of inspection points of the structure using a laser Doppler vibrometer or a interferometer coupled to an image capture device. In some examples, the method further includes generating an image or map of at least a portion of the inspection locations. In some examples, the method further includes separating foreground inspection targets from background objects using a mask formed by thresholding vibration responses based on the determined properties.

In other examples of the disclosed technology, a system for performing disclosed methods includes a measurement acquisition component coupled to one or more excitation sources configured to induce a structure to a steady state vibration response by applying a continuous vibrational signal to the structure and a processor coupled to the measurement acquisition component, the processor being configured to analyze data produced by the measurement acquisition component. In some examples the measurement acquisition component includes a laser Doppler vibrometer configured to measure velocity of a surface of the structure at a plurality of points in time by scanning a laser over an inspection area of the surface. In other examples, the measurement acquisition component includes an interferometer and image capture system configured to measure velocity of a surface at a plurality of points in time.

In some examples of the disclosed technology, the excitation sources include a piezoelectric transducer, an ultrasonic transducer, a repeating Q-switched laser, a vibrating platform, and/or a vibrating fixture. In some examples, the processor is configured to analyze the measurement acquisition data by isolating individual guided-wave modes in a transformed measurement matrix, decomposing the transformed measurement matrix according to a set of wavenumbers, generating a wavenumber amplitude field by calculating the amplitude of the decomposed transformed measurement matrix, and producing a wavenumber map.

In some examples of the disclosed technology, the system is configured to perform any of the methods disclosed herein. In some examples, one or more computer-readable storage media storing computer-readable instructions cause a computer to perform at least a portion of any of the disclosed methods.

The foregoing and other objects, features, and advantages of the invention will become more apparent from the following detailed description, which proceeds with reference to the accompanying figures.

BRIEF DESCRIPTION OF THE DRAWINGS

FIG. 4 illustrates two charts showing the real and imaginary parts of exemplary measurement data, as can be displayed in certain examples of the disclosed technology.

FIGS. 7A-7F illustrate charts depicting example measurement data as it is processed according to the system of FIG. 6.

FIG. 8 illustrates another exemplary method of determining properties of a structure, as can be implemented in certain examples of the disclosed technology.

DETAILED DESCRIPTION

I. General Considerations

Figure 1:
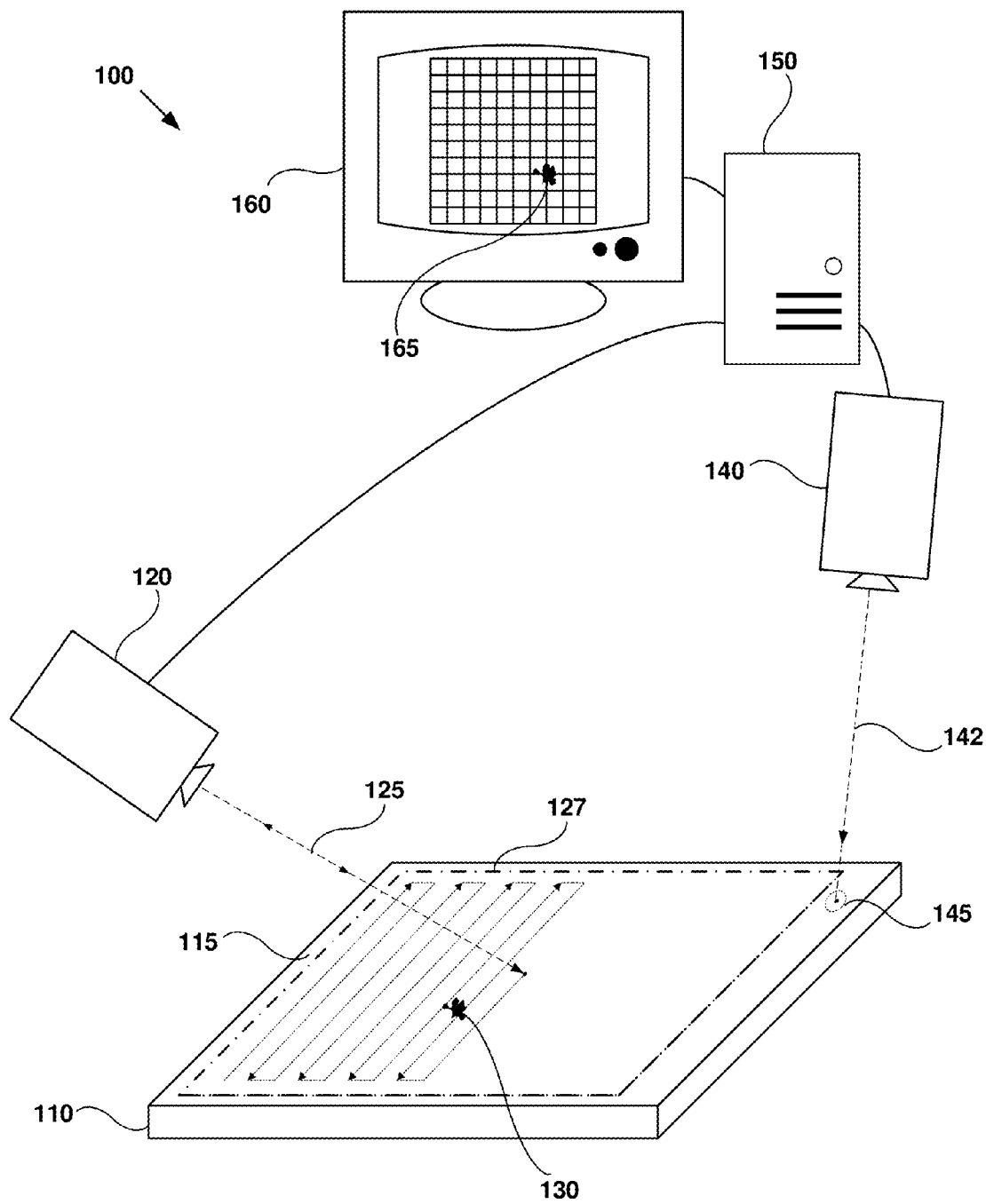
FIG. 1 illustrates an exemplary environment in which certain examples of the disclosed technology can be implemented.

This disclosure is set forth in the context of representative embodiments that are not intended to be limiting in any way.

As used in this application the singular forms "a," "an," and "the" include the plural forms unless the context clearly dictates otherwise. Additionally, the term "includes" means "comprises." Further, the term "coupled" encompasses mechanical, electrical, magnetic, optical, as well as other practical ways of coupling or linking items together, and does not exclude the presence of intermediate elements between the coupled items. Furthermore, as used herein, the term "and/or" means any one item or combination of items in the phrase.

The systems, methods, and apparatus described herein should not be construed as being limiting in any way. Instead, this disclosure is directed toward all novel and non-obvious features and aspects of the various disclosed embodiments, alone and in various combinations and sub-combinations with one another. The disclosed systems, methods, and apparatus are not limited to any specific aspect or feature or combinations thereof, nor do the disclosed things and methods require that any one or more specific advantages be present or problems be solved. Furthermore, any features or aspects of the disclosed embodiments can be used in various combinations and subcombinations with one another.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed things and methods can be used in conjunction with other things and methods. Additionally, the description sometimes uses terms like "produce," "generate," "display," "apply," "estimate," "analyze," and "determine" to describe the disclosed methods. These terms are high-level abstractions of the actual operations that are performed. The actual operations that correspond to these terms will vary depending on the particular implementation and are readily discernible by one of ordinary skill in the art.

Theories of operation, scientific principles, or other theoretical descriptions presented herein in reference to the apparatus or methods of this disclosure have been provided for the purposes of better understanding and are not intended to be limiting in scope. The apparatus and methods in the appended claims are not limited to those apparatus and methods that function in the manner described by such theories of operation.

Any of the disclosed methods can be implemented using computer-executable instructions stored on one or more computer-readable media (e.g., non-transitory computer-readable media, such as one or more optical media discs, volatile memory components (such as DRAM or SRAM), or nonvolatile memory components (such as flash drives or hard drives)) and executed on a computer (e.g., any commercially available computer, including smart phones or other mobile devices that include computing hardware). Any of the computer-executable instructions for implementing the disclosed techniques, as well as any data created and used during implementation of the disclosed embodiments, can be stored on one or more computer-readable media (e.g., non-transitory computer-readable media). The computer-executable instructions can be part of, for example, a dedicated software application, or a software application that is accessed or downloaded via a web browser or other software application (such as a remote computing application). Such software can be executed, for example, on a single local computer (e.g., as a process executing on any suitable commercially available computer) or in a network environment (e.g., via the Internet, a wide-area network, a local-area network, a client-server network (such as a cloud computing network), or other such network) using one or more network computers.

For clarity, only certain selected aspects of the software-based implementations are described. Other details that are well known in the art are omitted. For example, it should be understood that the disclosed technology is not limited to any specific computer language or program. For instance, the disclosed technology can be implemented by software written in C, C++, Java, or any other suitable programming language. Likewise, the disclosed technology is not limited to any particular computer or type of hardware. Certain details of suitable computers and hardware are well-known and need not be set forth in detail in this disclosure.

Furthermore, any of the software-based embodiments (comprising, for example, computer-executable instructions for causing a computer to perform any of the disclosed methods) can be uploaded, downloaded, or remotely accessed through a suitable communication means. Such suitable communication means include, for example, the Internet, the World Wide Web, an intranet, software applications, cable (including fiber optic cable), magnetic communications, electromagnetic communications (including RF, microwave, and infrared communications), electronic communications, or other such communication means.

II. Introduction to Certain Aspects of the Disclosed Technology

Exemplary methods and apparatus disclosed herein utilize continuous, steady, periodic excitation, for example, excitation of a specimen using a signal that is constructed from one or more single frequency periodic tones. As used herein, a "steady" signal's energy is distributed substantially regularly in time, in contrast to repeated, short-duration burst signals, which, while periodic over a long enough time interval, involve short concentrations of energy in time. As used herein, periodic signals include those that are composed of one or more periodic tones with irrational frequencies, which are mathematically aperiodic, but considered periodic in practice.

In certain examples where the specimen-under-test is maintained at a steady-state response when scanning, pausing between inspection points can electively be avoided. In some examples, the scanning system employed does not require stopping at each inspection point; instead, the scanning signal continuously sweeps along a specified path across the scan region, mapping the one-dimensional string of measured values to the scan area according to the control parameters of the scanning mechanism. In some examples, an entire inspection area may also be measured simultaneously using a system that can capture multiple spatial samples at once, such an interferometer with a CCD camera. In some examples of the disclosed technology, since energy is being continuously pumped into the system, leading to a much larger vibration response relative to pulsed excitation, averaging is usually not necessary.

In some examples of the disclosed technology, steady state response at each point in the scan area can be represented by an amplitude and phase term at each component frequency of the excitation signal. From measurements of vibration of the specimen, estimates of instantaneous amplitude and phase are made for each component frequency, and for each inspection point in the structure. These estimates at each component frequency effectively remove, from the measurement, vibrations other than those at the excitation frequencies, significantly reducing measurement noise and increasing system immunity to natural, low-frequency vibrations in the inspected specimen. This can allow inspections to be performed while the inspected system is still online and in service.

Certain methods and apparatus disclosed herein can be used to visualize variations in a structure under test, including but not limited to, for example, manufacturing variations and defects, damage, variations in thickness or composition, and other properties of the structure through rapid, full-field measurements of the structure's steady-state response to a steady, periodic ultrasonic excitation. Taking measurements of a structure's relatively high amplitude steady-state response enables significantly faster scans by avoiding many of the signal-to-noise ratio issues typically associated with existing scanned ultrasonic measurements.

A physical wave has two frequencies: a temporal frequency (often referred to as just "frequency") and a spatial frequency (often referred to as "wavenumber"). Temporal frequency is the rate at which a wave oscillates over a progression of time. Wavenumber is the rate at which a wave oscillates over a progression of space. Reference to a wave's "wavenumber," can equivalently refer to "wavelength" or "wave phase velocity," since these properties are mathematical manipulations of one another. More specifically, wavelength equals 1 divided by wavenumber, and wave phase velocity equals frequency divided by wavenumber.

Resonant ultrasound spectroscopy and acoustic interferometry utilize temporal frequency for non-destructive inspection of a sample. In a similar fashion, certain technologies disclosed herein utilize spatial frequency (wavenumber) for inspection of a sample. In some examples of the disclosed technology, this is done by making automated estimates, on a spatial point-by-point basis, of the frequency-, wave-mode-, and orientation-dependent wavenumber and wave amplitude of the sample.

In some examples of the disclosed technology, a steady, periodic signal, which is constructed from one or more ultrasonic periodic tones with frequencies $f_1$, $f_2$, etc., is continuously applied to an "inspection target" through some mechanism of transduction, bringing the structure to a steady-state vibration response. The response to this excitation is measured over an "inspection area" through some form of scanning or direct imaging.

In some examples of the disclosed technology, the measured response is analyzed as follows. For each composing excitation frequency, the amplitude and phase of the response at that frequency is estimated at each point in the inspection area using scanning or direct imaging. The response at each frequency is decomposed according to a set of wave-modes, wavenumbers, and/or wave orientations.

The wave amplitude is computed as a function of wavenumber for each inspection point, frequency, wave-mode, and/or wave orientation. This forms a set of wavenumber signatures. For a given frequency, wave-mode and/or wave orientation, this forms a three dimensional field of wavenumber signatures over the inspection area: wave amplitude versus wavenumber, x-coordinate, and y-coordinate.

The presence of material in contact with an inspected specimen effectively alters the structure of the specimen, and in turn, the wave attributes. As such, the technique may be used to map the distribution of material contents and estimate material phase and properties.

In some examples of the disclosed technology, the three dimensional field may be reduced to a two-dimensional image or map by extracting, at each spatial coordinate, the dominant wavenumber (wavenumber with the highest wave amplitude).

In some examples of the disclosed technology, the complex-shaped inspection targets in the foreground may be separated from objects in the background using a mask formed by thresholding the amplitudes of the decomposed responses.

III. Exemplary Environment in which Certain Disclosed Methods can be Performed FIG. 1 is a schematic representation 100 of a suitable environment in which certain embodiments of the disclosed technology can be practiced. As shown in the schematic representation 100, a sample 110 having a top surface 115 is illuminated by a measurement acquisition component 120. As shown FIG. 1, the measurement acquisition component 120 includes a Laser Doppler Vibrometer (LDV) configured to make a full field response measurement. As shown, the LDV (measurement acquisition component 120) scans a laser in a periodic sweeping pattern across the top surface 115 of the sample 110.

The LDV of the measurement acquisition component 120 emits a laser beam 125 in a scanning pattern back and forth across the top surface 115 of the sample 110. The LDV measures shift in frequency of light reflected from a target, which in turn is can be used to measure a velocity of the target at the incident point of the light upon the target.

Light from the laser beam 125 emitted by the measurement acquisition component 120 onto the top surface 115 of the sample 110 is partially reflected back into the LDV, where it can be compared to a reference signal and, in turn, by measuring Doppler shift in the beam, be used to measure velocity at the current inspection point. As shown in FIG. 1, the laser beam 125 is scanned within the boundaries of an inspection area 127 on the top surface 115.

Also shown in FIG. 1 is a defect 130 in the sample 110 which may be located underneath the top surface 115 of the sample 110, for example, in the interior of the sample, or on the obverse side of the top surface 115 of the sample 110.

In other examples of the disclosed technology, including those described in further detail below, the LDV used in the illustrated measurement acquisition component 120 can be replaced by, or supplemented with, additional forms of scanning technology. For example, an air-coupled transducer can be used measure the response at a number of inspection points from a distance of up to few centimeters from the surface of the inspection area. The air-coupled transducer is physically moved over the surface structure, following a scanning pattern to obtain a series of measurements.

In some examples of the disclosed technology, multiple, overlapping scans may be stitched together by matching the wave pattern in the overlapping regions. For example, the measurement acquisition component 120 can be combined with a three-dimensional (3-D) scanning system, such as LIDAR (Laser Illuminated Detection And Ranging) systems, to map measurements to automatically-generated 3-D representations.

Also shown in FIG. 1 is an excitation source 140. Here, the excitation source 140 is a Q-switched laser configured to excite the surface of the target by emitting a pulsed laser beam 142 onto the top surface 115 of the sample 110. As shown, the beam is aimed to strike a portion 145 of the top surface 115 inside or outside of the inspection area 127. Thus, the excitation source 140, can induce a steady state vibrational response in the sample 110 without contacting the sample itself.

In other examples of the disclosed technology, a transducer (e.g., a piezoelectric or other suitable ultrasonic transducer) is physically affixed to the scanning surface, an obverse surface, or another portion of the sample 110, and remains fixed during inspection. One such example is discussed below regarding FIG. 9. The transducer can be affixed temporarily for use during testing, or in other examples, the transducer can be permanently affixed to the target surface. Positioning of the excitation source(s) can be arbitrary, so long as sufficient vibration energy reaches the inspection area. In some other examples, multiple transducers can be employed in order to achieve a desired steady state response in the sample 110. Examples of suitable excitation sources, that can be used in particular applications of the disclosed technology include temporarily affixed transducers, permanently installed transducers, vibrating platforms, vibrating fixtures, sound waves, or repeating Q-switched lasers. Non-laser excitation techniques frequently confer the benefit of not requiring an expensive and dangerous high-power laser while still enabling remote, less-invasive inspection.

As will be readily understood to one of ordinary skill in the art, the measurement acquisition component 120 and the excitation source 140 can be replaced or supplemented with other suitable technologies in other examples.

Data acquired using the measurement acquisition component 120 can be further processed, for example, using the technologies described in further detail below. The data is processed using a computer 150 and results, including maps of the processed data, can be viewed on an attached display 160. An image 165 of the defect 130 stands out in the wavenumber estimate map depicted on the attached display 160.

The spatial shape in each region of the inspection area, defined by local amplitude and phase information derived from the measured vibration at a number of inspection points within the inspection area 127, is decomposed, using combined time, space, frequency, and wavenumber transforms, into to a set of waves. Each of the waves has its own amplitude, phase, wavenumber, orientation, and frequency attributes. The combined set of these decomposed wave attributes is unique to the local properties and/or structure of the specimen. Each small region over which these wave attributes are extracted can be treated as a single spatial sample, or "pixel," and formed together with other pixels to create a map, or "image," of the scanned area. For example, for continuous scanning, a set of properties measured over a distance Δx is assigned to a pixel. The wave attributes may be imaged directly or first converted to specimen and/or structure properties using techniques and apparatus detailed further below. As the wave attributes are time-independent, this allows the attributes to be extracted using steady-state responses to non-synchronized, arbitrarily-placed excitation sources.

In some examples, a structure under test is excited to a steady-state with a single tone excitation, f, and the response is measured, in the form of a time history, at each a number of inspection point in a uniform rectangular grid of spatial sampling points. This results in an N by M by T three-dimensional (3-D) measurement matrix v [x, y, t] that is indexed according to the spatial (x, y) and temporal (t) samples. Assuming the structure is vibrating within the bounds of linearity, this measurement can take the form:

$$v[x,y,t]=a[x,y]\cos(2\pi ft)+b[x,y]\sin(2\pi ft)+n[x,y,t] \quad \text{(Eq. 1)}$$

where n [x, y, t] is considered to be the noise of the measurement. In this example, the response measured at each spatial point is synchronized to the same point in time in the excitation cycle, so that all spatial measurement points are phase-synchronized. In examples where this assumption is not true, the phase of each response can be shifted accordingly. From a measurement, a pair of maximum likelihood estimates for a(x, y) and b(x, y) can be obtained according to $$\hat{a}[x,y]=\text{Re}(c[x,y]) \text{ and } \hat{b}[x,y]=Im(c[x,y]) \quad \text{(Eq. 2)}$$

where $$c[x,y] = \frac{1}{T}\sum_{t=0}^{T} v[x, y, t]\exp(-j2\pi f(t-\tau[x, y])) \quad \text{(Eq. 3)}$$

where τ is the time interval between the starts of neighboring scan points, which is equal to T for an uninterrupted measurement stream. This is the time-domain discrete Fourier transform of the signal at the excitation frequency f. For steady-state excitation, the two-dimensional (2-D), complex-valued matrix c[x, y] contains the relevant response information. Individually, the real and imaginary parts, a[x, y] and b[x, y] can be thought of as two snapshots in time of the steady-state response separated by 90° temporal phase, as depicted in FIG. 4 for a sample measurement of an aluminum plate. As shown in FIG. 4, the real 400 and imaginary 410 components of a distributed steady-state response measurement are plotted on an x-y axis for an aluminum plate.

In some examples, the measurement matrix c[x, y] is acquired as follows. A single tone ultrasonic excitation at frequency f is applied to the structure, for example, through an affixed piezoceramic disk. This excitation is generated substantially without interruption during the entire scan period to maintain the structure at a steady-state response. For example, when using an LDV as the scanning technology, the LDV laser scans at a specified speed over the discretized 2-D grid of spatial sampling points, while the analog-to-digital converter (ADC) digitizes the sensed response as a single stream of values. Following the scan, the measurement is broken into the 3-D matrix, v [x, y, t], of equal-sized time blocks corresponding to each spatial sample point, and the inner product along the time dimension is computed according to Equation 3 above, resulting in the final complex-valued measurement matrix c[x, y].

Synchronization is not necessary between the excitation source 140 and measurement acquisition component 120, such that the two systems can be independent. This independence allows the excitation source(s) to be built into the inspected system and simply switched on during inspection, in certain embodiments. Synchronization is also not necessary when multiple excitation sources are employed.

Figure 2:
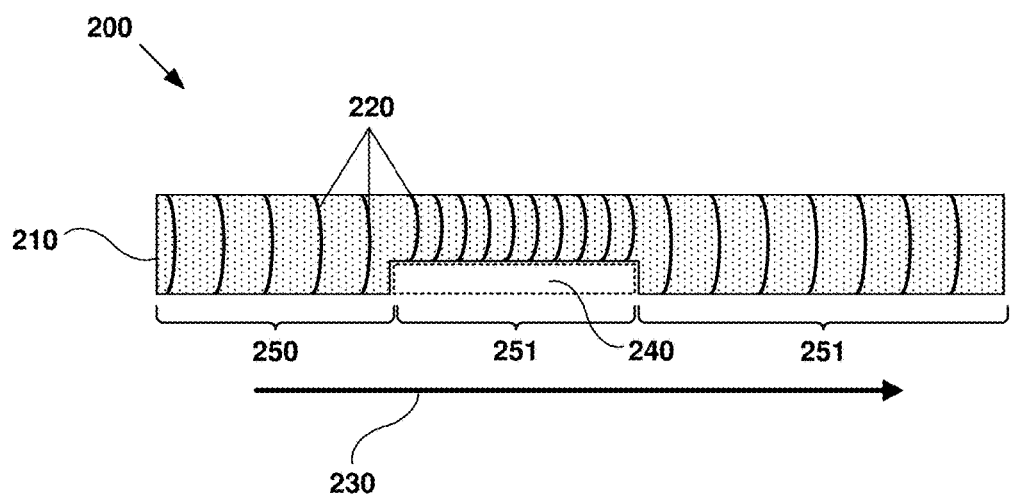
FIGS. 2 and 3 are diagrams illustrating wave propagation through two different specimens.

FIG. 2 is a simplified, not-to-scale, cross-sectional diagram 200, of a first exemplary, substantially planar specimen 210 under test, using the system illustrated and described above regarding FIG. 1. As shown as FIG. 2, a Lamb wave is propagating through the specimen 210 in the direction indicated by the arrow 230. The Lamb wave 220 propagates through three different portions 250-252 as illustrated. As shown in FIG. 2, an area of damage including a defect 240 is indicated by a dashed rectangle, where a void has formed on one side of the specimen 210. The wave number of the Lamb wave changes as it propagates in the portion 251 of the specimen 210 near the defect 240. Because of the reduced thickness in the portion 251 near the defect 240, the wave number, in this case, increases in that section of the specimen. Thus, by observing changes in wave number measured when the specimen 210 is excited by a continuous steady signal, the damaged area with the defect 240 can be detected.

Figure 3:
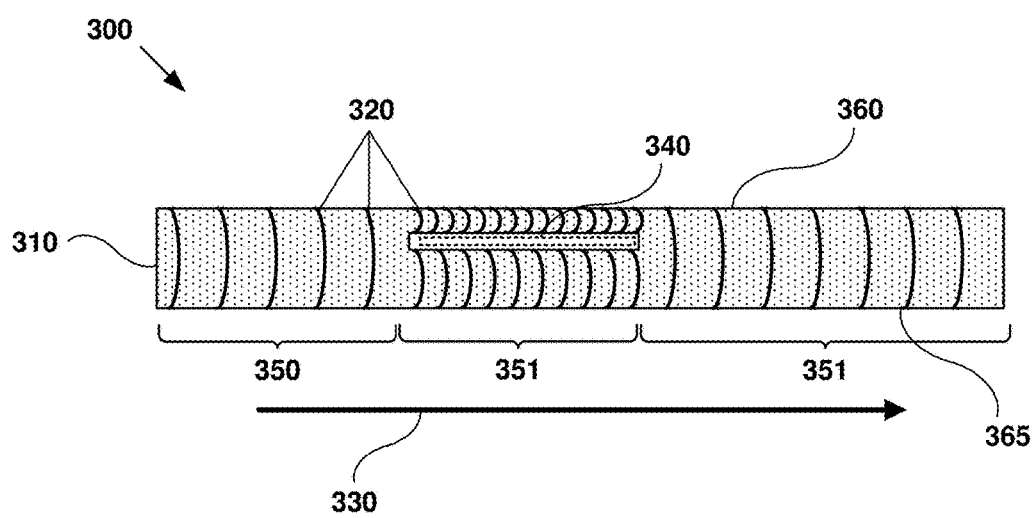

FIG. 3 is a simplified, not-to-scale, cross-sectional diagram 300, of a second exemplary, substantially plainer specimen 310 under test, using the system illustrated and described above regarding FIG. 1. In contrast to the specimen 210 under test shown in FIG. 2, the specimen 210 in FIG. 3 is a composite material that exhibits delamination within its interior. As shown in FIG. 3, a Lamb wave 320 is propagating through the specimen 310 in the direction indicated by the arrow 330. The wave number of the Lamb wave 320 varies at it passes through three different portions 350-352 of the composite material of the specimen 310. A damaged area 340, where the composite material is delaminating, is indicated by a dashed rectangle. The wave number of the Lamb wave increases as it propagates through the portion 351 of the specimen 310 exhibiting delamination in the damaged area 340. Of note is that the wavenumber observed will vary depending on whether the surface of the specimen 310 is observed from the top surface 360 or the obverse surface 365 of the specimen 310. In a similar fashion to that discussed above regarding FIG. 2, these defects can be observed using the apparatus of FIG. 1 even though they may not be observable from either surface 360 or 365 of the specimen 310.

As will be explained further below, the system depicted in FIG. 1 can be readily adapted to a number of different applications and environments. Data attained using the measurement acquisition component 120 can be processed in a manner that will allow for rapid analysis to determine the wave number at a number of different inspection points on the surface of the sample 110.

Figure 5:
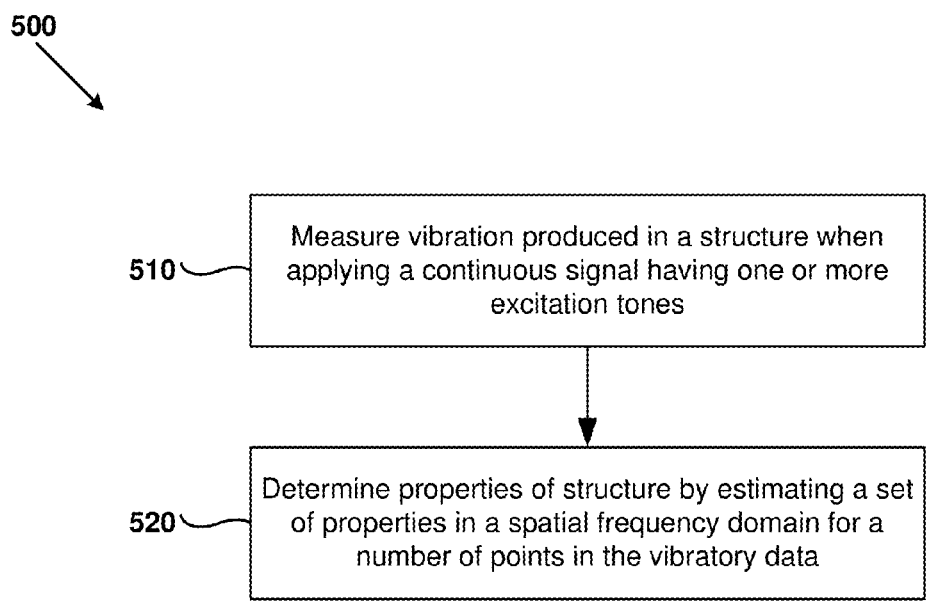
FIG. 5 illustrates an exemplary method of determining properties of a structure.

IV. Exemplary Method of Measuring and Processing Data According to the Disclosed Technology FIG. 5 is a flow chart 500 outlining an exemplary method of measuring and processing data as can be practiced in some examples of the disclosed technology. The outlined method can be practiced using the environment further described above with respect to the schematic representation 100 of FIG. 1.

At process block 510, a scanning apparatus, such as an LDV or an interferometer coupled to an image capture device, is used to measure vibration produced in a structure as a continuous periodic signal is applied. The continuous signal has one or more excitation tones of a fixed frequency. The measured vibration is captured in a 3-D matrix v [x, y, t]. Data in the measured vibration matrix is sent to a computing device for further processing to determine the properties of the structure at process block 520.

At process block 520, the properties of the structure, including defects or damage, can be determined by estimating a set of properties in the spatial frequency domain for the measured data received from process block 510. A number of points in the 3-D matrix v are converted to the spatial frequency domain for analysis. Based on this analysis, discontinuities or variation in the response of the structure from the applied steady frequency can be isolated and used to determine variations in the structure. Additional examples of how to perform the processing to determine properties at process block 520 are elaborated in further detail below.

Figure 6:
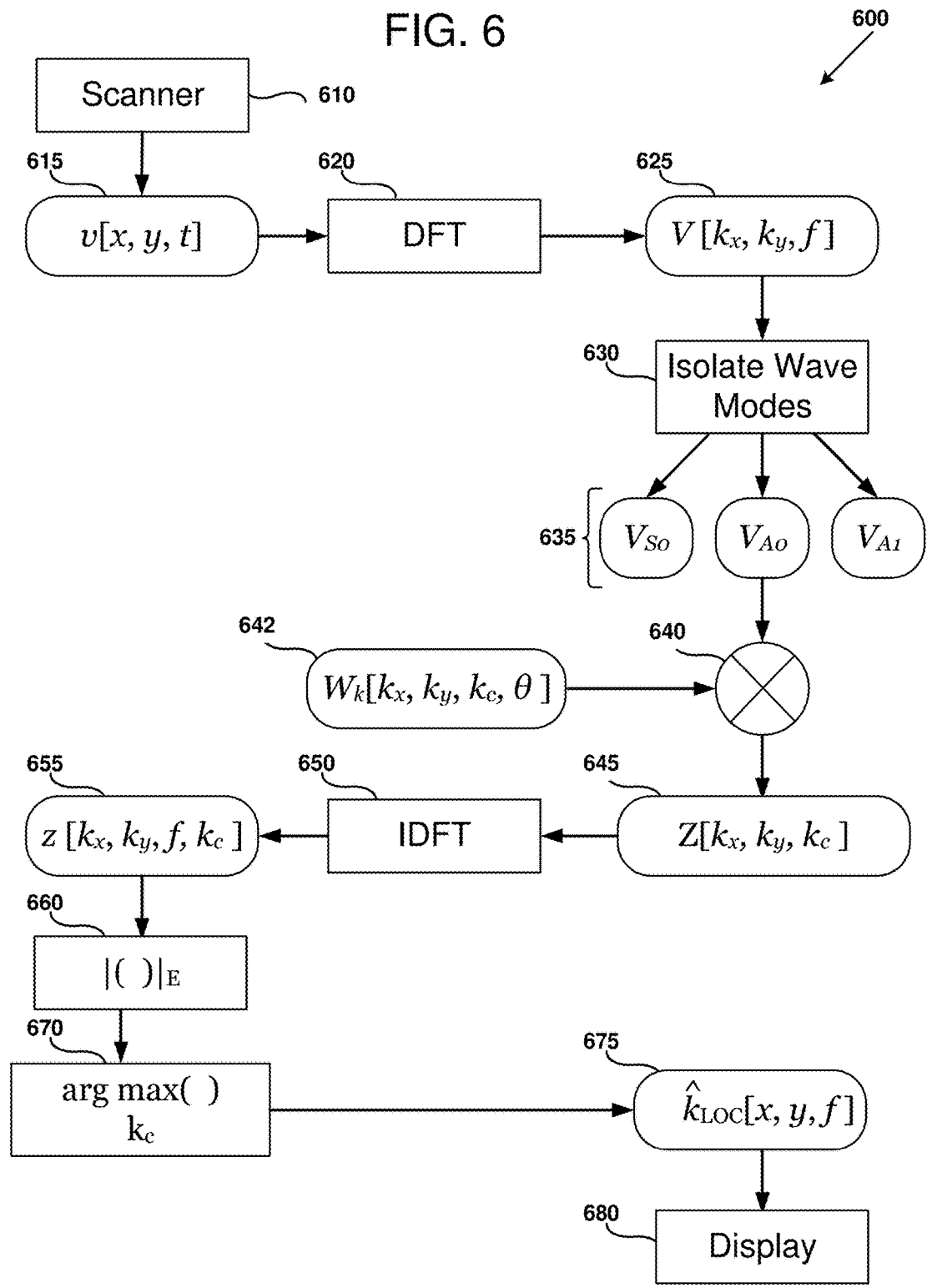
FIG. 6 is a system diagram illustrating processing of measurement data, as can be implemented in certain examples of the disclosed technology.
Figure 7A:
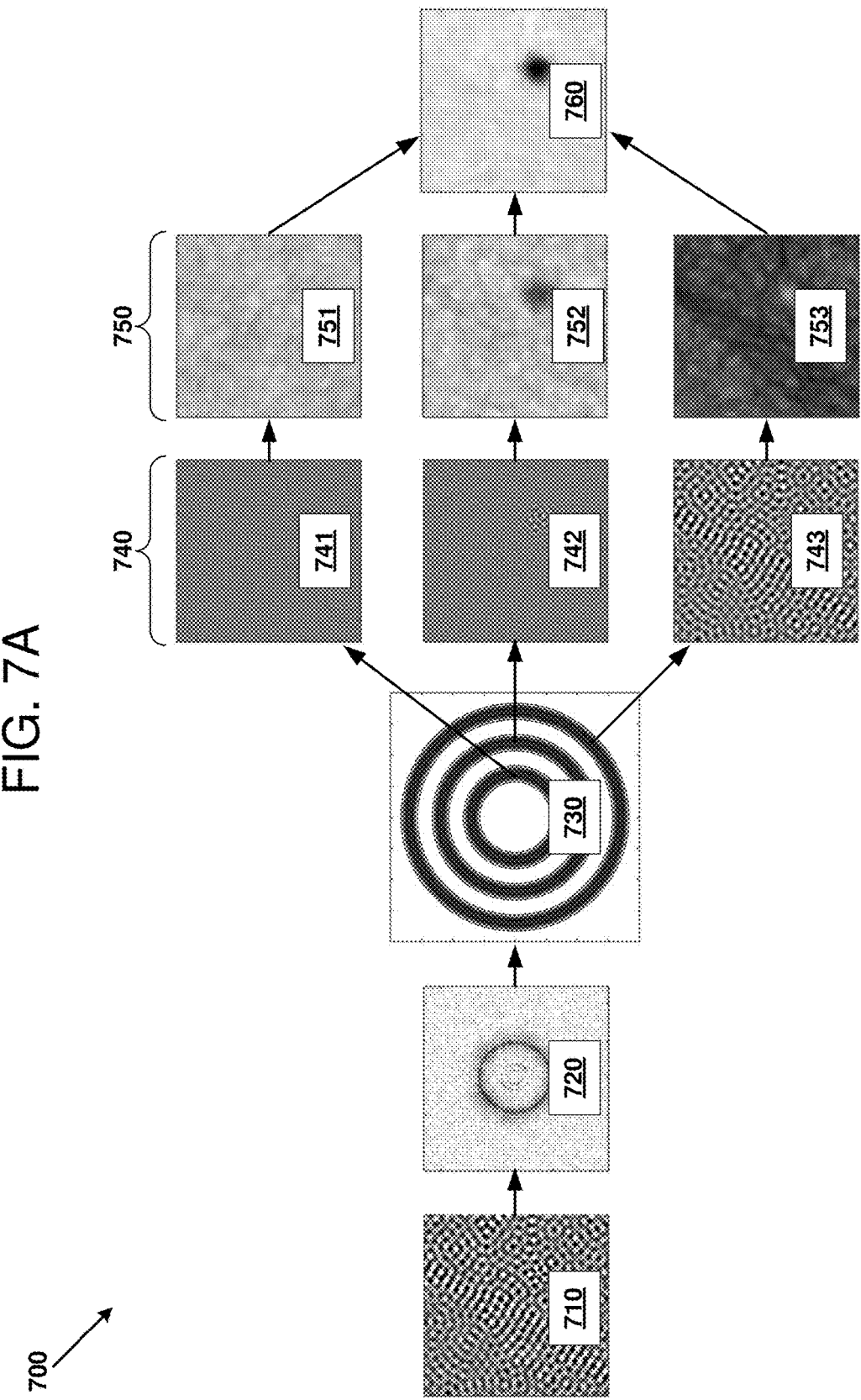

V. Exemplary Analysis of Scanning Data According to the Disclosed Technology FIG. 6 is a block diagram 600 illustrating data flow through a system as a number of operations performed in analyzing scanning data, as can be practiced in some examples of the disclosed technology. FIGS. 7A-7F are graphs of data resulting from manipulations to measurement data according to a method of analyzing scanning data, as can be performed using the system of FIG. 6. In particular, FIG. 7A is a block diagram 700 presenting an overview of processing of example measurement data (e.g., analyzing of scanning data) with the system of FIG. 6. The example measurement data of FIG. 7A are further detailed in FIGS. 7B-7F and the following description.

A. Generation of Measurement Data

As shown in FIG. 6, a measurement acquisition device 610 (e.g., the LDV depicted in FIG. 1) is used to produce wave response measurements by generating measurement data that is indexed according to the spatial and temporal samples. For example, an LDV can generate measurement data for a specimen-under-test as it is being excited to a steady-state response using an appropriate excitation source (for example, the excitation source 140 as described above).

The measurement data can be collected as follows. The test structure is excited to and held at a steady-state response. This excitation can be performed by generating, through some means of transduction, a steady, periodic excitation signal which is composed of one or more ultrasonic tones with frequencies $f_1$, $f_2$, etc. The excitation may be provided, for example by a temporarily affixed transducer, a permanently installed transducer, a vibrating platform or fixture, or a repeating Q-switched laser. In some examples, a transducer is in physical communication with the test structure. In other examples, the transducer communicates with the test structure through a medium (e.g., a gas or liquid between the transducer and the test structure). In most applications, it is desirable that this excitation is generated without interruption throughout the entire scan/imaging period so that the structure remains at a steady-state response.

For scanning-based collection, a scanning LDV, air-coupled transducer, or other scanning acoustic/ultrasonic measurement system can be configured to scan continuously over a specified scan path covering the desired scan region, while an analog-to-digital converter (ADC) digitizes the sensed response as a single stream of values, $v_0[t]$. In some examples, the LDV generates a frequency-modulated signal that is demodulated according to the source frequency to derive the measure velocity values $v_0[t]$.

For imaging-based collection, an imaging interferometer or other full-field measurement system collects a series of snapshots of the vibration response $v_1[x, y, t]$. The timing and quantity of the snapshots are selected such that the response at each excitation tone can be independently determined. The imaging-based approach generally requires that there be at least twice as many snapshots as there are tones, and that the timing between snapshots is such that the aliased response frequencies do not overlap or approach zero.

The measurement acquisition device 610 emits measurement data 615 that can be expressed as a three-dimensional matrix ($v[x, y, t]$) of velocity data indexed by x-y coordinate over the target surface over a temporal time range t. For example, the surface 115 of the sample 110 can be mapped to coordinates x-y.

Velocity measurements taken at various times are collected and then sent to a mapping module 620 for further processing. The time domain data obtained from the scanner can be transformed to the spatial frequency domain using any number of suitable methods. For example, discrete Fourier transform can be applied to generate spatial frequency domain values.

B. Example Method of Mapping Steady State Excitation Responses to a Spatial Frequency Domain The measurement data 615, whether expressed as a single stream of measurement values, $v_0[t]$, or series of snapshots, $v_1[x, y, t]$, is then mapped by a spatial domain mapping module 620 to produce spatial frequency response data 625. For example, the measurement data 615 can be used to generate a two-dimensional matrix of complex response values, $c_1[x, y]$, which contains the relevant response information. This is done for at least one, if not all of the composing excitation frequencies (e.g., in the case of multiple tones having different excitation frequencies) to produce a 3-D spatial response matrix $V[k_x, k_y, f]$. The magnitude and phase of these complex values correspond to the amplitude and phase of the steady state response at that point in the scan area for the corresponding frequency.

There are a number of ways to perform this mapping using the mapping module 620, including the Fourier transform approach and the analytic signal approach.

For the Fourier transform approach to mapping the scanning data, the single stream of values is broken into a set of blocks, where each block corresponds to a spatial coordinate in the scan area. This forms a three-dimensional matrix $v_1[x, y, t]$. When using an imaging approach to collecting the measurement data 615, this matrix is already collected directly. The complex steady state response for each spatial coordinate is then estimated according to $$c_1[x, y] = \frac{1}{T}\sum_{t=0}^{T} v_1[x, y, t]\exp(-j(2\pi f)(t - \tau)) \quad \text{(Eq. 1)}$$

where T is the length, in time, of each block and τ is the time delay between blocks. Thus, this is the time-domain discrete Fourier transform of the signal at the excitation frequency f, synchronized to the same point in the excitation cycle. For measurement data 615 obtained using a scanning approach, τ is equal to T. For measurement data 615 obtained using an imaging approach, τ is equal to zero.

$$c[x,y]=\hat{a}[x,y]+j\hat{b}[x,y] \quad \text{(Eq. 2)}$$

Figure 7B:
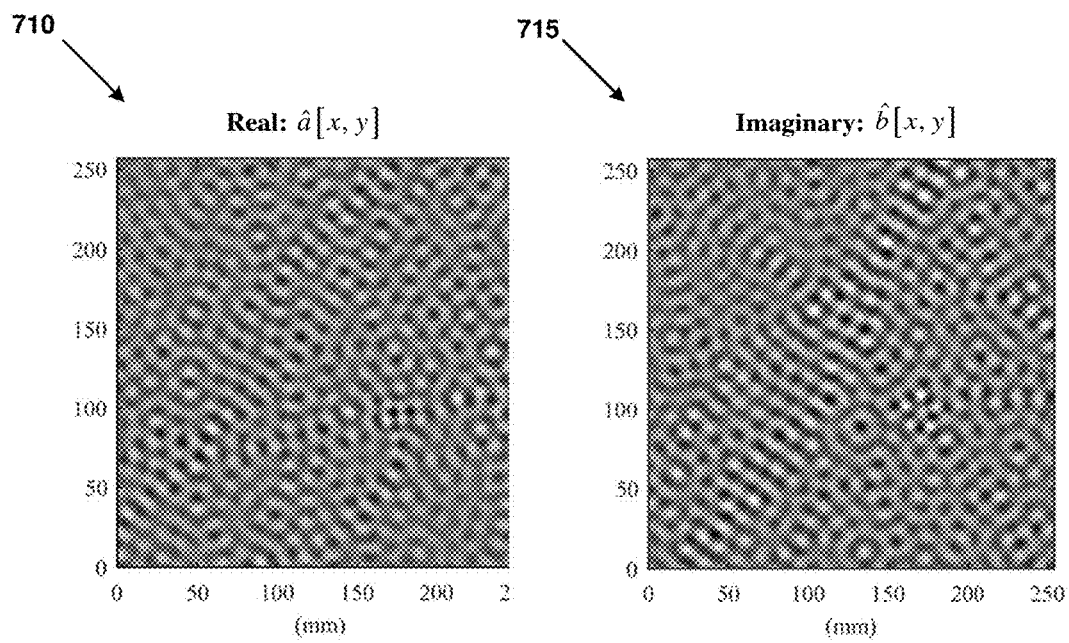

FIG. 7B includes two graphs of data corresponding to an example of measurement data obtained using, for example, the measurement acquisition device 610. The measured complex steady state response $c_1[x, y]$ of an example plate structure undergoing steady, continuous excitation is plotted in charts 710 and 715. The x-axis and y-axis correspond to x-y inspection locations on the plate, and the intensity of the magnitude of the steady-state response is indicated by shading. This complex steady state response, as decomposed into its constituent real and imaginary parts is also plotted in the chart 710, which chart illustrates the real portion of the complex steady state response $c_1[x, y]$, and in chart the 715, which chart illustrates the imaginary portion of the complex steady state response $c_1[x, y]$.

For the analytic signal approach, instead of treating the measurement as a set of time-blocks corresponding to each spatial coordinate, the measurement data can be treated as a single series of time samples. The entire measurement is filtered using a narrow-pass-band filter with center frequency f. Next, the analytic signal of each of the filtered measurements, $v_A[t]$, is calculated. This produces a single stream of complex values. To phase synchronize the measurements, the stream is phase-shifted according to the following equation:

$$c_0[t]=v_A[t]\exp(-j(2\pi f)t) \quad \text{(Eq. 3)}$$

These phase-synchronized values are then mapped back to the discretized grid of spatial sampling points according to the known scan path to produce the complex response matrix $c_1[x, y]$.

Figure 7C:
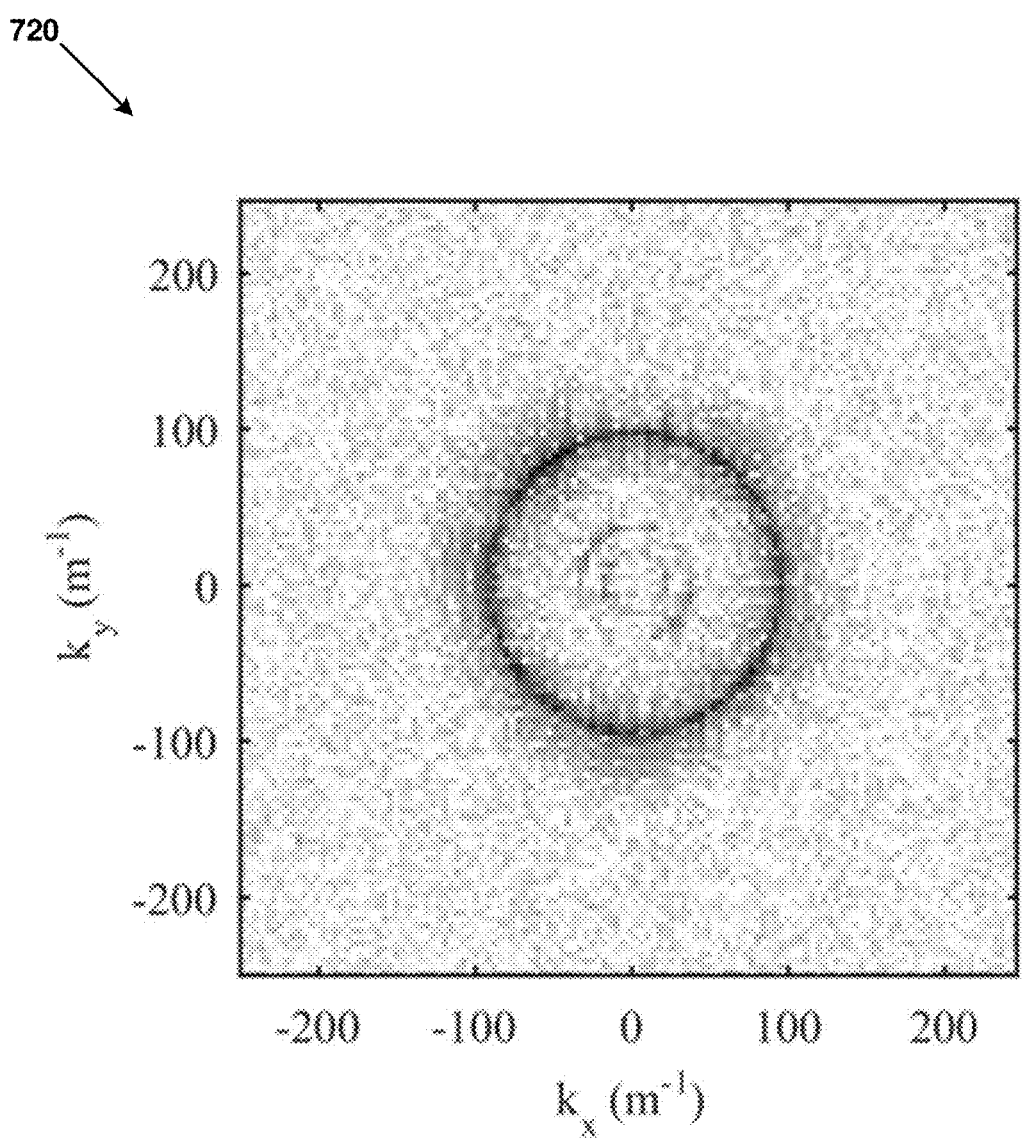

When exciting a specimen using more than a single tone, the response will be a superposition of individual single-tone responses. The complex response, $c_1[x, y]$, can then be extracted for each tone according to the Fourier transform approach, the analytic signal approach, or some other approach. This will produce a three-dimensional response matrix, $c_2[x, y, f]$, with the third dimension corresponding to excitation frequency. FIG. 7C illustrates an example chart 720 of a three-dimensional response matrix generated by applying a discrete Fourier transform to the complex steady state response data illustrated in the charts 710 and 715. As shown in FIG. 7C, the x-axis and y-axis correspond to wavenumber $k_x$ and $k_y$, and the intensity of the response in the spatial frequency domain is indicated by the shading intensity.

Whether the Fourier transform approach, analytic signal approach, or other suitable approach is used by the mapping module 620 to produce the mapped data 625, the mapped data is further processed to produce two-dimensional maps, or images, of local wavenumber estimates. One objective of the processing is to estimate the spatial-wavenumber-dependent wave amplitude response for one or more component frequenc(ies) f and over a set of coordinates (x, y) in order to form a set of three-dimensional wavenumber amplitude fields over at least a portion of the imaging region. Another objective of the processing is to estimate the dominate wavenumber at each set of coordinates (x, y) in order to form a two-dimensional wavenumber map. This processing is outlined below in the following subsections: (C) isolate individual guided-wave modes in the transformed measurement matrix; (D) decompose the transformed measurement matrix according to a set of wavenumbers; (E) produce a wavenumber amplitude field by calculating the amplitude of the decomposed results; and (F) produce a wavenumber map by determining, for at least a portion of the spatial points, the wavenumber that maximizes the amplitude field in the inspection area.

C. Example Method of Wave Mode Isolation

The steady state response of the structure under test is a superposition of all of the wave modes observed at each excitation frequency. However, processing can be simplified by processing individual wave modes separately. In the frequency ranges typical LDVs are capable of measuring, the zero-order symmetric (S0) and anti-symmetric (A0) Lamb wave modes are prominent. In those examples where the LDV (e.g., measurement acquisition component 120) measures velocity in the same direction as the beam (e.g., beam 125), then it will be significantly more sensitive to the A0 mode, which is primarily out-of-plane at low frequencies. In these examples, the S0 mode can be removed using a high-pass wavenumber filter, since the A0 mode will exist at a higher wavenumber.

Each individual wave mode can be isolated as follows, using a wave mode isolation module 630, although it will be readily understood by one of skill in the art that other suitable methods can be used. FIG. 6 depicts the wave mode isolation module 630 isolating three guided wave modes 635 from the mapped data 625, $V_{S0}$ (zero-order symmetric wave mode), $V_{A0}$ (zero-order asymmetric wave mode), and $V_{A1}$ (first-order asymmetric wave mode). In other examples, a different number of wave modes can be selected for isolation and further analysis, as will be readily understood to those of ordinary skill in the art. Although an infinite number of wave modes exist in the steady state response, practically speaking, the number of wave modes that can be measured is around ten such wave modes.

In the wavenumber domain, for a single frequency, the wave mode will trace an ellipse-like path centered at the origin. Each wave mode can then be isolated by applying a window in the frequency domain that bounds the path. The wave mode isolation can be automated, for example, by finding a peak in the wavenumber domain, tracing a path around the ellipse by following high-amplitude neighbors, and applying a window about the traced path.

In practice, the peak in the wavenumber intensity diagram will usually be a point on the ellipse that corresponds to the A0 mode. The radial wavenumber $k_R$ can then be determined:

$$k_R = \sqrt{k_x^2 + k_y^2} \qquad \text{(Eq. 4)}$$

The A0 mode is then determined by applying high-pass filter with a cutoff value equal to one-half of the radial wavenumber $k_R$.

This is repeated for each wave mode, generating a matrix of complex maps C[x, y, f, m], which matrix is additionally indexed by wave-mode m. In some examples, processing time is reduced by generating a partial number of complex maps C[x, y, f, m]. For example, only the A0 mode might be isolated in some examples of the disclosed technology.

D. Wavenumber Decomposition Process

As shown in FIG. 6, the isolated guided wave mode(s) are produced as a filtered measurement matrix $V[k_x, k_y]$ generated by the wave mode isolation module 630, which matrix in turn is sent to a bank 640 of narrowband wavenumber filters. As shown in FIG. 6, the wavenumber filter bank 640 accepts a 3-D matrix describing a set of narrowband filters to apply, indexed by wavenumber $k_c$. A relatively large number of filters (e.g., from 50 to 100 wavenumber bands) can be applied to the isolated wave modes 635. The number of filters applied and corresponding frequency can be adjusted to tradeoff processing time versus accuracy. For example, if little damage/corrosion in a sample under test is expected, a smaller number of wavenumber filters can be used to improve processing time. Conversely, if a greater amount of damage/corrosion is expected, a larger number of wavenumber filters can be used.

One way to perform the narrowband filtering operation is to apply a set of radially symmetric Gaussian windows in the wavenumber domain according to the equation:

$$Z[k_X, k_Y, k_C] = V[k_X, k_Y] W[k_X, k_Y, k_C] \qquad \text{(Eq. 5)}$$

where the window function for center wavenumber $k_c$ is provided by the equation:

$$W[k_X, k_Y, k_c] = \exp\left(-\frac{\left(\sqrt{k_X^2 + k_Y^2} - k_C\right)^2}{0.72 B_K^2}\right) \qquad \text{(Eq. 6)}$$

and $B_K$ is the half-power bandwidth of the filter. For example, in FIG. 7D, chart 730 illustrates three window functions, diagrams 731-733. For the illustrated example, the diagrams 731-733 are based on the three window functions created using a common half-power bandwidth $B_K$ value set to 30 m$^{-1}$ and center wavenumbers $k_c$ of 70, 120, and 170 m$^{-1}$, respectively.

In alternate examples of the disclosed technology, at least some of the isolated individual guided wave mode matrices are decomposed according to wavenumber, k, and, in some examples, wave orientation, θ, to obtain the decomposition matrix $c_4$[x, y, k, θ, f, m]. In the case of decomposition according to wave orientation, the window function described in Equation 6 is expanded according to $$W[k_X, k_Y, k_c] = \exp\left(-\frac{\left(\sqrt{k_X^2 + k_Y^2} - k_C\right)^2}{0.72 B_K^2} - \frac{\left(\tan^{-1}\left(\frac{k_X}{k_Y}\right) - \theta_C\right)^2}{0.72 B_\theta^2}\right) \qquad \text{(Eq. 7)}$$

where $θ_c$ are center wave angles and $B_θ$ is the half-power bandwidth with respect to wave angle.

The decomposition matrix 645 can be generated by passing the filtered measurement matrix $c_3$[x, y, f, m] through a bank of narrowband wavenumber filters. The filters are divided by wavenumber and orientation through windowing in the wavenumber domain according to the matrix operation:

$$C_4[k_X, k_Y, k, \theta, f, m] = C_3[k_X, k_Y, f, m] W[k_X, k_Y, k, \theta] \qquad \text{(Eq. 8)}$$

where $C_3[k_X, k_Y, f, m]$ is the Fourier transform of $c_3$[x, y, f, m] along the two spatial dimensions and $W[k_X, k_Y, k, θ]$ is a two-dimensional window 642 in the wavenumber domain centered at wavenumber k and orientation θ. In the case where the specimen is isotropic (or even approximately isotropic), such that wave propagation properties are independent of orientation, the orientation component of the filter can be ignored, leaving a rotationally symmetric wavenumber-domain window.

Since filtering in the Fourier domain is substantially equivalent to convolution in the spatial domain, the decomposition can alternatively be performed in the spatial domain through convolution with an appropriate set of wavenumber-centric and wave orientation-centric two-dimensional signals.

Figure 7D:
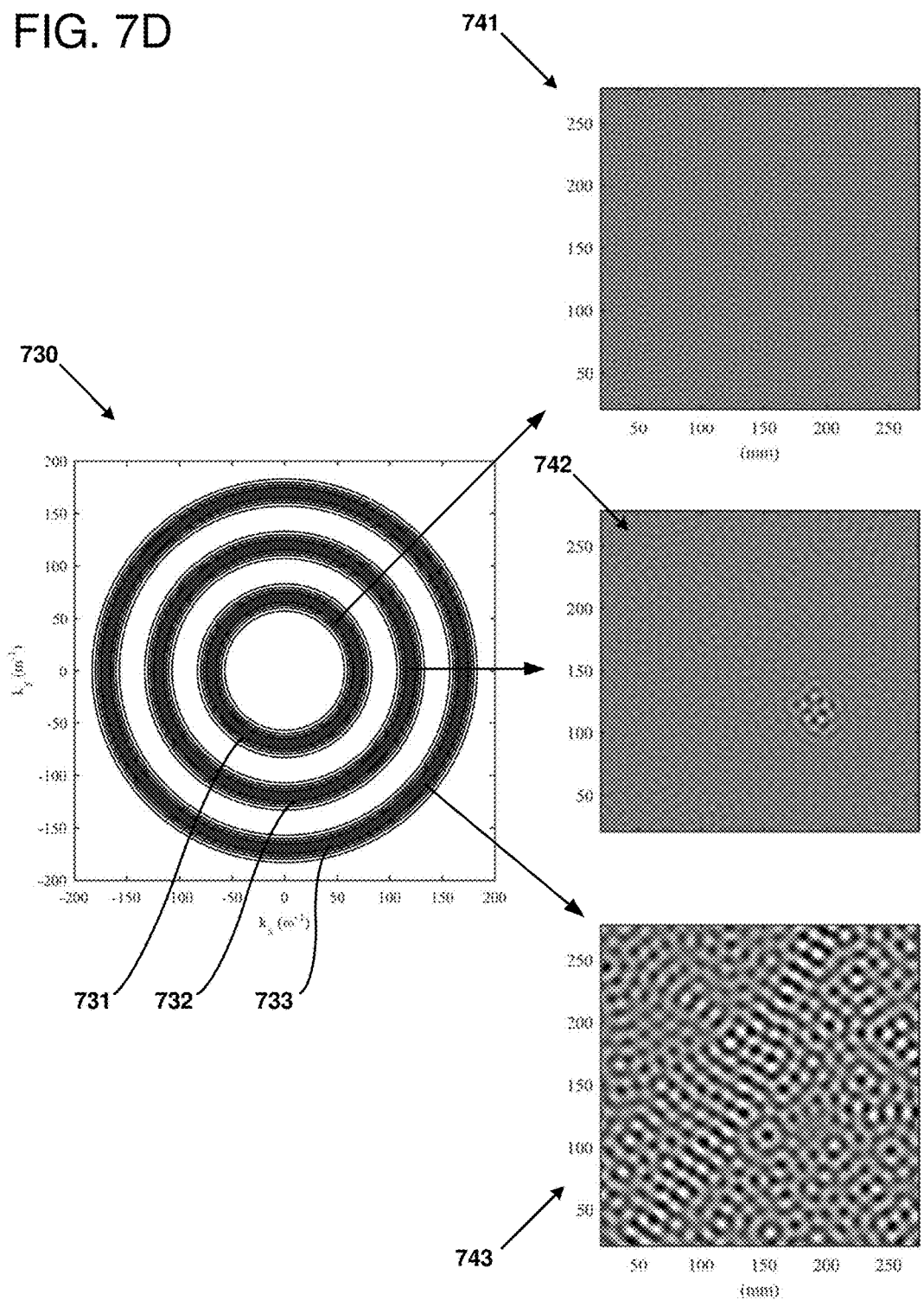

A set 740 of charts 741-743 of FIG. 7D illustrate examples of spatial-domain filter results $c_4$[x, y, k, θ, f, m] of measured data illustrated in the charts 710 and 715 after applying the three filter bank components, 731-733, at center wavenumbers $k_c$ equal to 70 m$^{-1}$, 120 m$^{-1}$, and 70 m$^{-1'}$, respectively. In these example cases, the measurement is not decomposed according to angle. It should be understood that charts 741-743 illustrate the real component of the spatial-domain filter results.

F. Calculated Wave Amplitude

After generating the decomposition matrix 645 (e.g., $Z[k_X, k_Y, k_c]$ or $C_4[k_X, k_Y, k, θ, f, m]$ discussed above at subsection V.D), wave amplitude fields are generated. Wave amplitude fields can be generated by calculating the wave amplitude for each spatial coordinate, wavenumber, wave orientation (if applicable), frequency (if applicable), and wave mode (if applicable) in the decomposed response. To obtain the wave amplitude, the wave envelope is calculated across the two spatial dimensions, where the wave oscillations occur.

Such wave amplitude generation can be performed for one-dimensional signals using the instantaneous amplitude according to the magnitude of the analytic signal. A similar procedure can be performed on 2-D signals using the monogenic signal, which is an extension of the analytic signal to multi-dimensional space. The (now) three components of the monogenic signal for a single one of the decomposed results are (leaving off the frequency, orientation, and wave-mode dependency for ease of presentation):

$$P[k_X, k_Y] = Z[k_X, k_Y], \quad \text{(Eq. 8)}$$

$$Q_X[k_X, k_Y] = \frac{-jk_X}{\sqrt{k_X^2 + k_Y^2}} Z[k_X, k_Y], \quad \text{(Eq. 9)}$$

$$Q_Y[k_X, k_Y] = \frac{-jk_Y}{\sqrt{k_X^2 + k_Y^2}} Z[k_X, k_Y] \quad \text{(Eq. 10)}$$

Following an inverse Fourier transform back to the spatial domain using an inverse mapping module 650, the spatial envelope can be calculated according to $$a[x, y] = \sqrt{p[x, y] * p[x, y] + q_X[x, y] * q_X[x, y] + q_Y[x, y] * q_Y[x, y]}, \quad \text{(Eq. 11)}$$

where p[x, y]* indicates the scalar complex conjugate. For a given orientation, frequency and mode, this produces a three-dimensional field 655 of wave amplitudes, which can be viewed as a series of two-dimensional slices along wavenumber, forming a set of images, or altogether as an animation progressing through the wavenumber dimension.

FIG. 7E includes a set 750 of three charts that plot the magnitude (751-753) at $k_C$=70, 120, and 170 m$^{-1}$ for the narrowband filtered matrices discussed above (741-743).

Note the region (757) of higher wave amplitude in this particular wavenumber band. This region corresponds to a thinner region in the specimen (plate) used to generate the measurement values. The local wavenumber is expected to be different from the remainder of the plate (in this example around 96 m$^{-1}$ instead of 82 m$^{-1}$).

G. Dominant Wavenumber and Amplitude Estimation Process

After generating a three-dimensional field 655 of wave amplitudes, a space-wavenumber representation 660 of the measurement matrix in the form of a set of envelope maps is generated. In some examples, the space-wavenumber representation of the measurement matrix is in the form of a set of amplitude maps, each corresponding to a different wavenumber, component frequency, and wave mode, (a[x, y, k, θ, f, m]). To generate a two-dimensional map for a given orientation, frequency, and mode, the amplitude-maximizing wavenumber for each spatial coordinate is determined, which is referred to as the wavenumber estimate $k_{Est}$ 670. The wavenumber estimate 670 can be calculated as follows:

$$k_{Est}[x, y, \theta, f, m] = \underset{k_C}{\operatorname{argmax}}\, a[x, y, k_C, \theta, f, m] \quad \text{(Eq. 12)}$$

Subsequently, the amplitude at each coordinate, wave orientation, frequency component, and wave mode is the envelope evaluated at a maximizing wavenumber 675:

$$a_{Est}[x, y, \theta, f, m] = a[x, y, k_{Est}, \theta, f, m] \quad \text{(Eq. 13)}$$

Figure 7F:
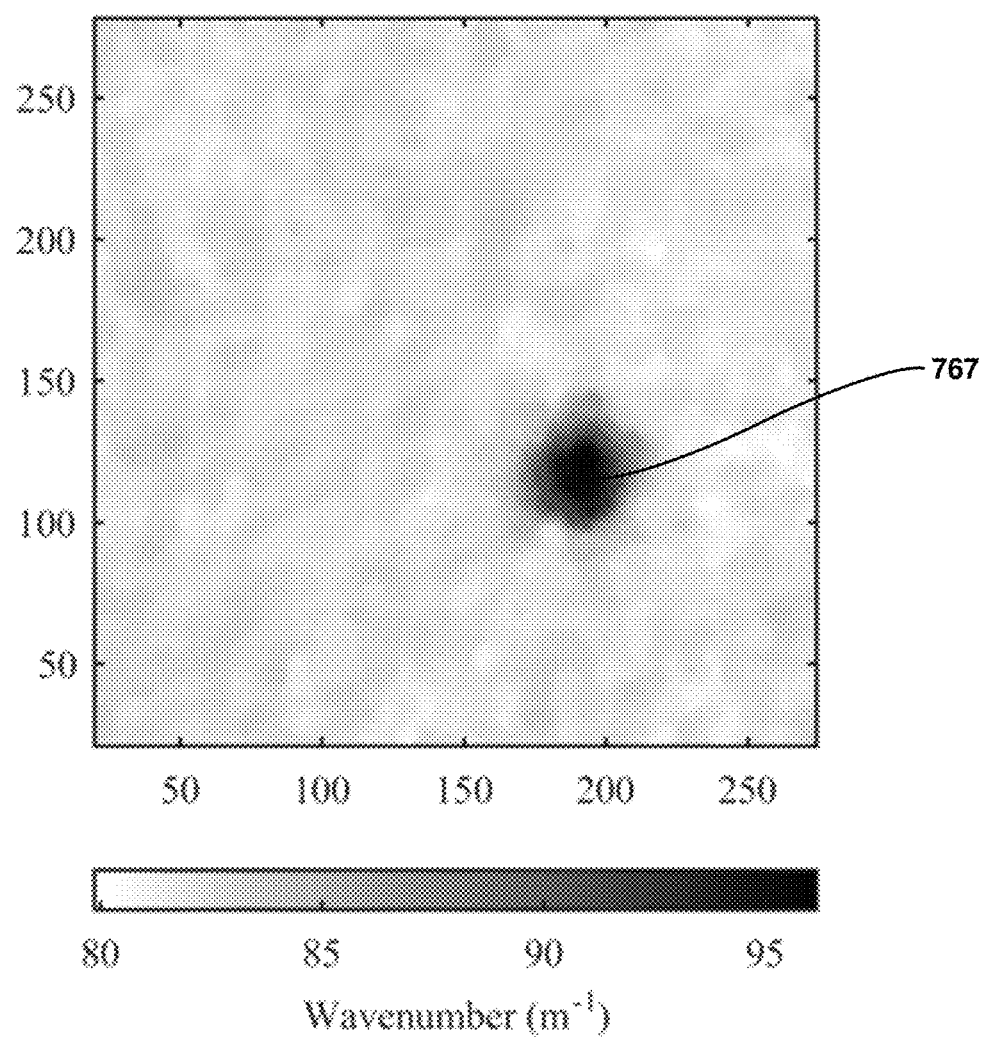

An example of a map generated for a maximizing wavenumber 675 is shown in the wavenumber map 760 of FIG. 7F. Note the region (767) of higher wave amplitude in this particular wavenumber band. This region 767 corresponds to a thinner region in the specimen (plate) used to generate the measurement values. Thus, for a given orientation, frequency, and wave mode, the results can then be viewed as two-dimensional maps, or images, of local wavenumber estimates, for example, using a computer display 680.

H. Background Masking Process

During a scan of a regularly shaped area, complex shaped specimens in the foreground can be automatically separated from objects behind the specimen using the specimen's response to the excitation, which is applied to the specimen but not to objects in the background. This is done by masking spatial inspection regions, or "pixels," that do not have measured vibration energy matching the pattern of the excitation source. The mask can be generated, for example, by taking the spatial wave amplitude/envelop matrix and summing across the wavenumber, orientation, frequency, and mode dimensions. The mask is then thresholded using statistics of the same measure of known background measurements, or by fitting a binomial distribution to the foreground-plus-background measurement and drawing a threshold between the two distribution modes. An example of results obtained using such a masking process is described below regarding FIG. 13.

As can be seen, use of the disclosed technology allows for the extraction of local wave propagation properties using steady, periodic ultrasonic excitation and continuous-scan sensing or direct imaging to enable non-invasive, high-rate, high-resolution, ultrasonic imaging.

VI. Exemplary Method of Analyzing Properties of a Structure

FIG. 8 is a flow chart 800 outlining an exemplary method of determining the physical properties of a structure, as can be used in some examples of the disclosed technology. The illustrated method can be used with, for example, the exemplary system outlined regarding FIG. 1 above, or the exemplary system discussed below regarding FIG. 9.

At process block 810, a periodic signal having one or more continuous excitation tones is applied to a structure under test. For example, the periodic signal can be applied using a piezoelectric transducer, or a Q-switched laser focused on a portion of the sample so as to cause ultrasonic vibration. In some examples, multiple transducers can be affixed to the structure, and in some examples, the transducers are either permanently or temporarily affixed to the sample. In some examples the excitation tones applied to the structure have frequencies substantially in the range of 30 to 500 kilohertz. In some examples multiple excitation tones are used while in others, a single excitation tone is applied to the structure. Regardless of the form of transducer used to excite the structure, once the structure has reached a steady-state vibrational response, the method proceeds to process block 820.

At process block 820, measurements of the steady state wave response of the structure for a number of inspection points within an inspection area of the structure are generated. In some examples, a laser Doppler vibrometer (LDV)

is used. In other examples an interferometer is used. The type of light used by the interferometer can vary depending on the requirements of a particular implementation, for example, the light can be: white light, or laser light, or light of a selected number of wavelengths. When an interferometer is used, an image capture device, such as a camera including a CCD (charge coupled device) or CMOS (complementary metal oxide semiconductor) sensor is used to collect snapshots of the vibrational response of the excited structure for a number of pixels within the inspection area at the same time. The measurements of the wave response can be expressed as a three dimensional matrix V indexed by x, y, and t, as discussed further above regarding FIG. 6. Once a number of measurements of the steady state wave response have been generated, the method proceeds to process block 830.

At process block 830, the measurements received from process block 830 are analyzed to determine steady state wave responses of the excited structure. In some examples of the disclosed technology, the analyzing comprises transforming at least a portion of the measurement data into spatial frequency domain data. In some examples, the analyzing comprises mapping the vibratory data to a two-dimensional matrix of complex response values. In some examples, the analyzing comprises isolating one or more individual guided wave modes from the spatial frequency domain data. In some examples, the analyzing further comprises decomposing the spatial frequency domain data according to a set of wave numbers. In some examples, the analyzing comprises producing a wave number amplitude by calculating amplitudes of the decomposed spatial frequency domain data. In some examples, the analyzing comprises producing a wave number by determining, for a number of inspection points in the measurement data, one or more wave number maxima for an amplitude field within the inspection area that was used to generate the measurement data.

In some examples, measurement data is transformed to the spatial frequency domain by calculating a time domain discrete Fourier transform of the data, while in other examples an analytic method is used to transform the measurement data. In certain examples, all or a portion of the analyzing can be performed in the time domain, as will be readily understood to one of ordinary skill in the relevant art.

In some examples of the disclosed technology, the analyzing of the wave response measurements at process block 830 can be performed using a general-purpose computer including a processor, memory, and computer-readable instruction stored on a computer-readable storage medium. In some examples, a specialized processor, ASIC (application specific integrated circuit), and/or an FPGA (field programmable gate array) are used to perform the analyzing. In some examples, the processing hardware is directly coupled to the measurement acquisition component, for example an LDV or interferometer, via a serial or network interface. In other examples, some or all of the analyzing can be performed on a remote server accessed via a computer network, such as a LAN (local area network) or the Internet. After the measurements have been analyzed, the method proceeds to process block 840.

At process block 840, physical properties of the structure are determined based on the analyzing performed at process block 830, including knowledge of the frequencies of one or more excitation tones that were used to excite the structure at process block 810. As will be readily understood to one of ordinary skill in the art, any number of applicable properties can be determined. For example, damage or variation in the structure under test including damage or variation not visible from the surface of the structure can be determined. In some examples, the properties of the structure itself, such as, but not limited to: material thickness, density, material composition, elasticity, material coating thickness, material coating adhesion, and/or temperature can be determined. Thus, the method illustrated in FIG. 8 can be applied to a number of practical applications, such as examining pipes in nuclear reactors or pipelines, analyzing damage in wind turbine blades, analysis of structures used in aerospace for example air frames and other suitable structures. The disclosed technologies are especially suited for applications that involve hazardous, high temperature and/or inaccessible environments where access to the structure under test is dangerous and/or expensive. Other applications of the disclosed technology include, but are not limited to, analysis of reusable space launch systems, manufacturing applications, etc.

Figure 9:
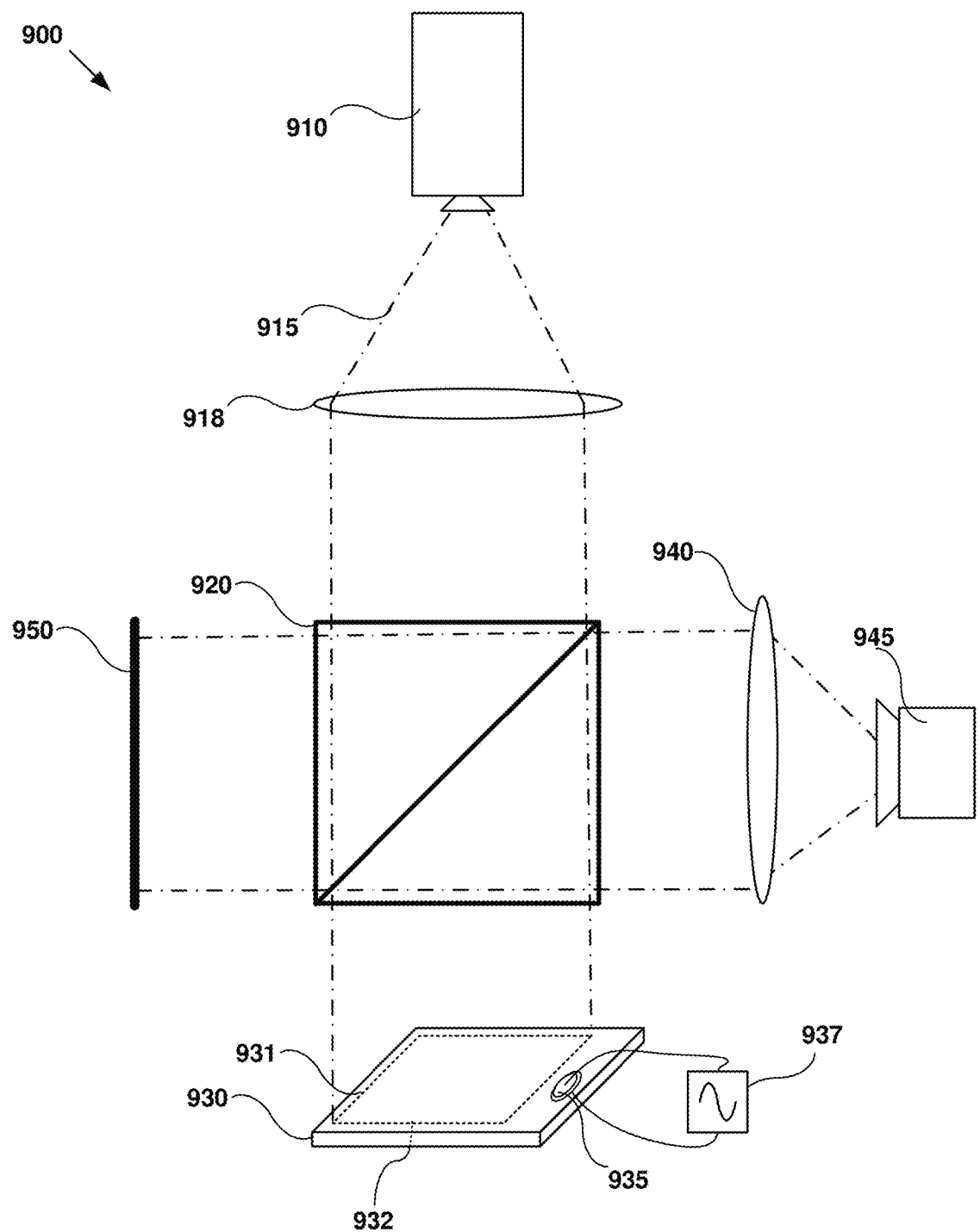
FIG. 9 illustrates an exemplary environment in which certain examples of the disclosed technology can be implemented.

VII. Exemplary Environment Using Image Capture Device and Piezoelectric Transducer FIG. 9 is a schematic diagram 900 of a suitable environment in which certain examples of the disclosed technology can be performed. As shown in FIG. 9, a light source 910, such as a laser, white light source, or other suitable light source projects light 915 through a beam expander and then on through a collimating lens 918. The collimated light in turn passes through a beam splitter 920 and a portion of the light from the collimating lens is projected onto a structure 930 under test within an inspection area 931 on the surface of the structure. As shown in FIG. 9, a piezoelectric transducer 935 is affixed to the top surface of the structure under test, outside of the inspection area 931. A sinusoidal wave source 937 is electrically connected to excite the transducer, which in turn excites the structure 930 to a steady state response. In other examples, the piezoelectric transducer 935 is affixed to the obverse surface 932 of the structure 930.

Light is reflected back from the structure 930 to the beam splitter 920 and then through a focusing lens 940 and into a measurement acquisition component 945 (as shown, an image capture device). The image capture device can be, for example, a CCD or CMOS camera. Also shown is a reference minor 950 which reflects a portion of the light received from the beam splitter 920 back through the focusing lens 940. Thus, while the arrangement displayed in the schematic diagram 900 generally corresponds to that of a Michelson interferometer, it will be readily apparent to one of ordinary skill in the art that any suitable imaging technology can be used, including those that utilize homodyne and heterodyne interferometry. Not shown in FIG. 9 are a computer, and computer display, which can be used to for example, analyze, map, and display data measured using the system illustrated in FIG. 9.

Synchronization is not necessary between the excitation source (e.g., transducer 935) and measurement acquisition component 945, such that the two systems can be independent. This independence allows the excitation source(s) to be built into the inspected system and simply switched on during inspection, in certain embodiments. Synchronization is also not necessary when multiple excitation sources are employed.

VI. Exemplary Computing Environment

Figure 10:
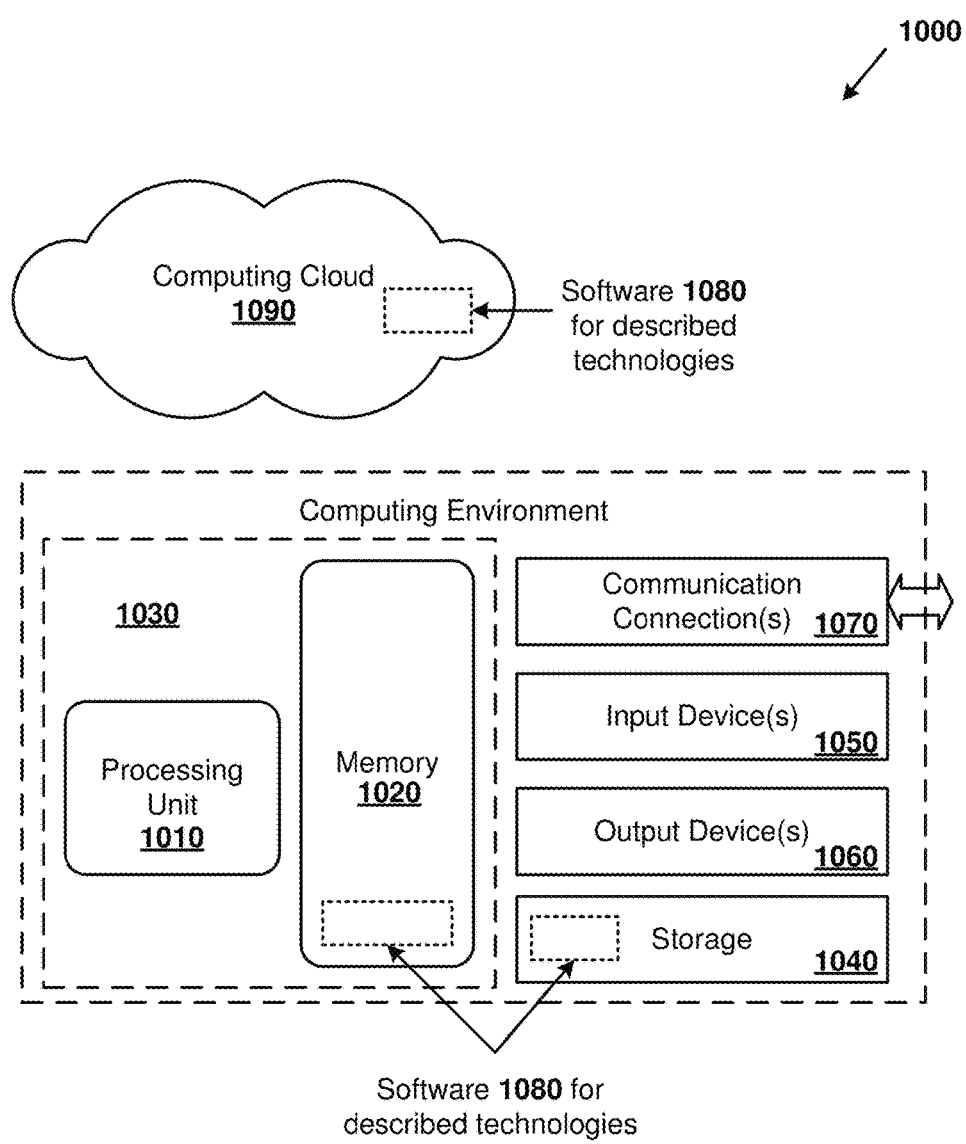
FIG. 10 illustrates an exemplary computing environment in which certain examples of the disclosed technology can be implemented.

FIG. 10 illustrates a generalized example of a suitable computing environment 1000 in which described embodiments, techniques, and technologies, including generating and analyzing measurement data, can be implemented. For example, the computing environment 1000 can implement all of the analysis functions described with respect to the block diagram 600 of FIG. 6, as described herein.

The computing environment 1000 is not intended to suggest any limitation as to scope of use or functionality of the technology, as the technology may be implemented in diverse general-purpose or special-purpose computing environments. For example, the disclosed technology may be implemented with other computer system configurations, including hand held devices, multiprocessor systems, microprocessor-based or programmable consumer electronics, network PCs, minicomputers, mainframe computers, and the like. The disclosed technology may also be practiced in distributed computing environments where tasks are performed by remote processing devices that are linked through a communications network. In a distributed computing environment, program modules may be located in both local and remote memory storage devices.

With reference to FIG. 10, the computing environment 1000 includes at least one central processing unit 1010 and memory 1020. In FIG. 10, this most basic configuration 1030 is included within a dashed line. The central processing unit 1010 executes computer-executable instructions and may be a real or a virtual processor. In a multi-processing system, multiple processing units execute computer-executable instructions to increase processing power and as such, multiple processors can be running simultaneously. The memory 1020 may be volatile memory (e.g., registers, cache, RAM), non-volatile memory (e.g., ROM, EEPROM, flash memory, etc.), or some combination of the two. The memory 1020 stores software 1080, images, and video that can, for example, implement the technologies described herein. A computing environment may have additional features. For example, the computing environment 1000 includes storage 1040, one or more input devices 1050, one or more output devices 1060, and one or more communication connections 1070. An interconnection mechanism (not shown) such as a bus, a controller, or a network, interconnects the components of the computing environment 1000. Typically, operating system software (not shown) provides an operating environment for other software executing in the computing environment 1000, and coordinates activities of the components of the computing environment 1000.

The storage 1040 may be removable or non-removable, and includes magnetic disks, magnetic tapes or cassettes, CD-ROMs, CD-RWs, DVDs, or any other medium which can be used to store information and that can be accessed within the computing environment 1000. The storage 1040 stores instructions for the software 1080 and measurement data, which can implement technologies described herein.

The input device(s) 1050 may be a touch input device, such as a keyboard, keypad, mouse, touch screen display, pen, or trackball, a voice input device, a scanning device, or another device, that provides input to the computing environment 1000. The input device(s) 1050 can also include interface hardware for connecting the computing environment to control and receive data from measurement acquisition components, control excitation sources, or to display data processed according to methods disclosed herein.

For audio, the input device(s) 1050 may be a sound card or similar device that accepts audio input in analog or digital form, or a CD-ROM reader that provides audio samples to the computing environment 1000. The output device(s) 1060 may be a display, printer, speaker, CD-writer, or another device that provides output from the computing environment 1000.

The communication connection(s) 1070 enable communication over a communication medium (e.g., a connecting network) to another computing entity. The communication medium conveys information such as computer-executable instructions, compressed graphics information, video, or other data in a modulated data signal.

Some embodiments of the disclosed methods can be performed using computer-executable instructions implementing all or a portion of the disclosed technology in a computing cloud 1090. For example, collection of measurement data can be executed in the computing environment (e.g., by the measurement acquisition component 120), while analysis of the measurement data can be performed on remote servers located in the computing cloud 1090 (e.g., by the general-purpose computer 150).

Computer-readable media are any available media that can be accessed within a computing environment 1000. By way of example, and not limitation, with the computing environment 1000, computer-readable media include memory 1020 and/or storage 1040. As should be readily understood, the term computer-readable storage media includes the media for data storage such as memory 1020 and storage 1040, and not transmission media such as modulated data signals.

VII. Experimental Results

FIGS. 11-14 illustrate a number of experimental results obtained using particular examples of the methods and apparatus disclosed herein. As understood to one of the ordinary skill in the art, such results illustrate certain advantages that can be realized in certain examples of the disclosed technology, but do not limit the scope of the claimed invention in any way.

The three specimens illustrated in FIGS. 11-13 and discussed below were scanned using a method disclosed above and according to the specific parameters listed below in Table 1. A higher excitation frequency was used in analyzing the composite specimens in order to achieve a higher nominal wavenumber for resolving the smaller structural features and defects. The scan rate was also reduced for the composite specimens to improve signal-to-noise ratio for the composite specimens and their corresponding smaller response amplitudes. All three specimens were scanned at a stand-off distance of three meters.

TABLE 1

| Specimen | Excitation Frequency (f) | Scanning Interval ($\Delta x$) | Scan Rate (S) |
| --- | --- | --- | --- |
| Aluminum | 100 kHz | 4.0 mm | 16 m/s |
| Projectile Impact (Composite) | 200 kHz | 1.5 mm | 6 m/s |
| Tool Drop (Composite) | 200 kHz | 1.0 mm | 4 m/s |

Both composite specimens (illustrated in FIGS. 12 and 13) were scanned over a rectangular inspection area encompassing the entire part. Regions of the scanned inspection area that were not excited by the transducer (regions that did not include the part), were then automatically removed by thresholding the spatial envelope of the full-field measurement, as discussed further above.

Figure 11:
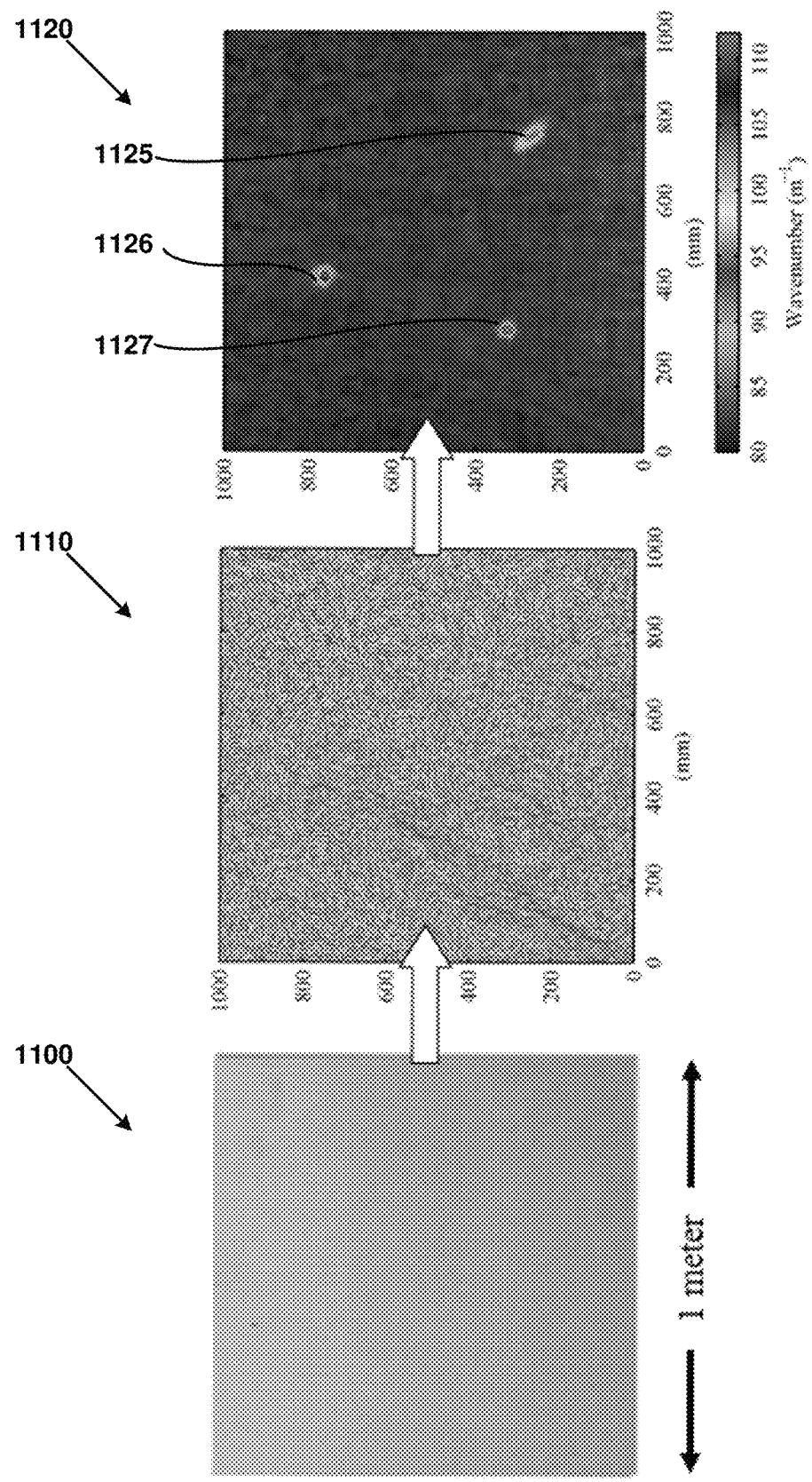
FIGS. 11-14 illustrate experimental results obtained using methods and apparatus disclosed herein.

FIG. 11 includes a photograph 1100 of 1.2 meter square aluminum panel. Three areas of corrosion of varying depth were induced on the surface opposite the scanning area. For the aluminum plate, a one meter by one meter subset of the part was scanned as the inspection area. The real part of a steady-state measurement is displayed in a chart 1110 and a final wavenumber estimate map 1120 is also displayed. As shown in the final wavenumber estimate map 1120, three imaged spots 1125-1127 match the locations and shapes of the actual corrosion spots to within three (3) mm, and the computed shift in wavenumber monotonically increases with corrosion depth.

Figure 12:
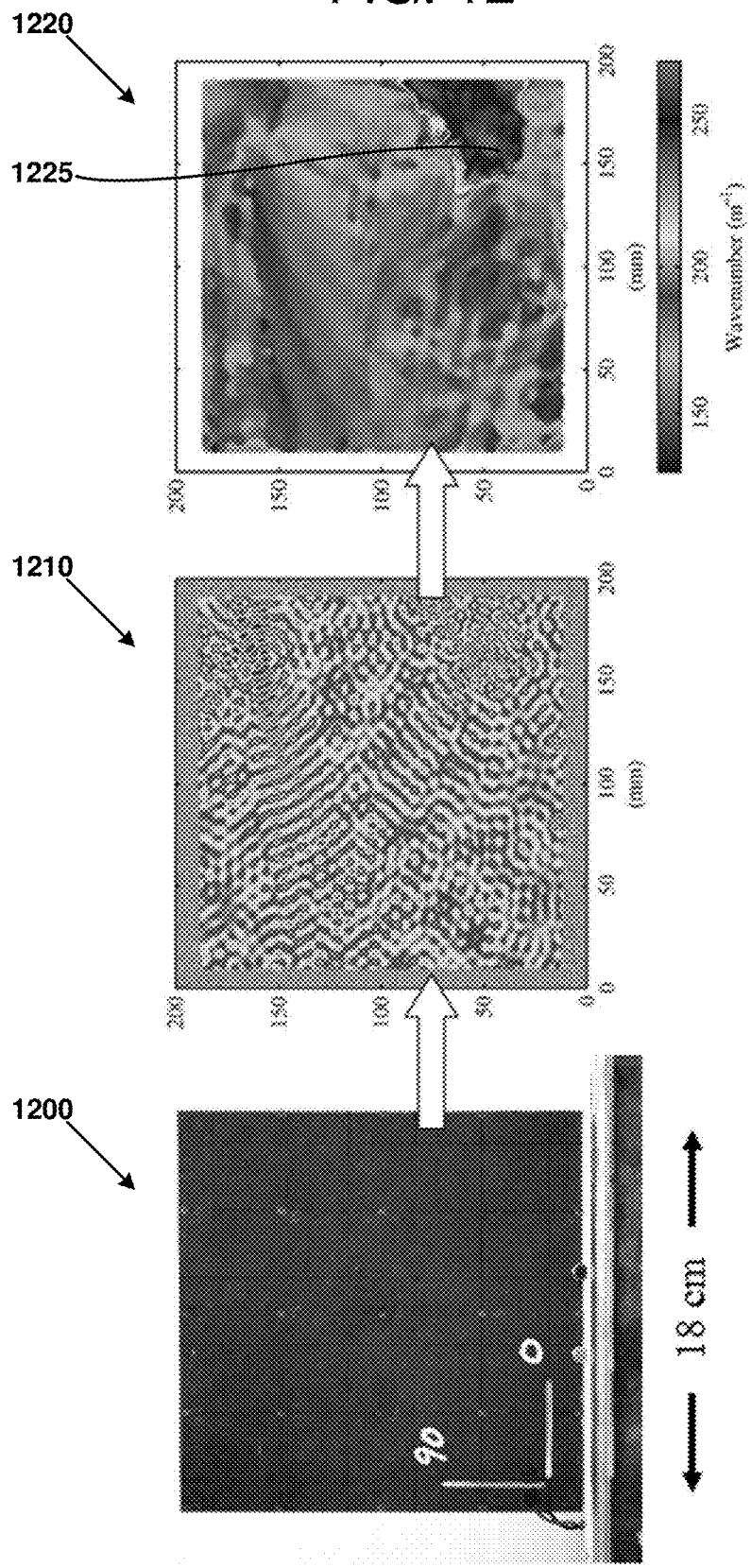

FIG. 12 include a photograph 1200 a first composite specimen having dimensions of approximately 180 mm on a side that has sustained a high-speed projectile impact, with damage (cracking) visible only on the surface obverse to the scanning area. The real part of a steady-state measurement is displayed in a chart 1210 and a final wavenumber estimate map 1220 is also displayed. As shown in the final wavenumber estimate map 1220, the imaged spot 1225 match the location and shape of the damage sustained from the projectile impact. The shift in wavenumber at the impact site was highest among all the damage modes. While the cracking on the opposite face only extends five (5) mm from the indicated impact location, it is clear from the image that the internal delamination propagated to the edge of the specimen.

Figure 13:
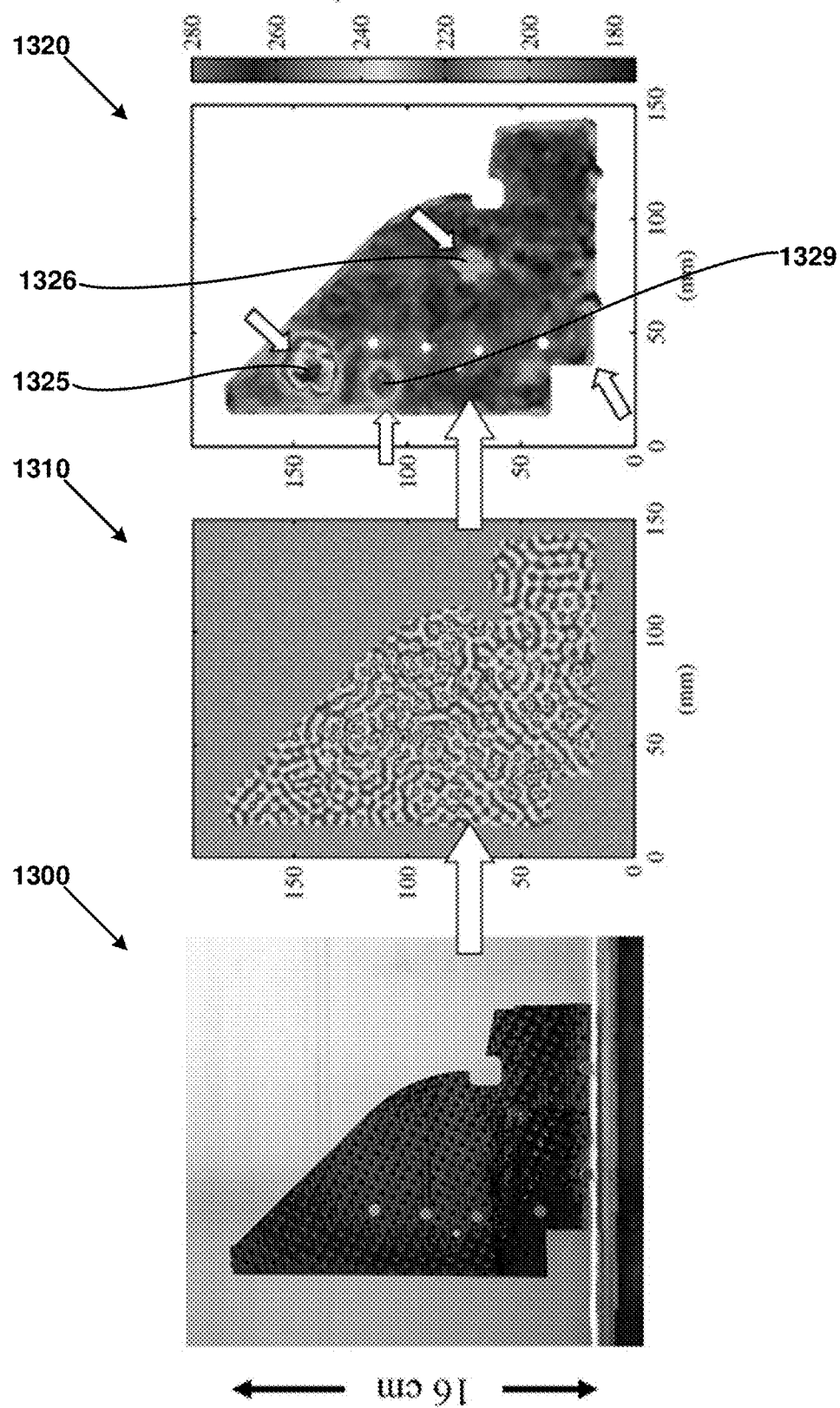

FIG. 13 includes a photograph 1300 of a second composite specimen having dimensions of 160 mm on a side that was subjected to two simulated "tool-drops" or slow-speed impacts, with no visible damage on either surface. The real part of a steady-state measurement is displayed in a chart 1310 and a final wavenumber estimate map 1320 is also displayed. The data obtained from scanning was subjected to the masking process disclosed above at Part V.H to remove background data. As shown in FIG. 13, the two impact locations 1325 and 1326 and the transducer location 1329 stand out in the final wavenumber estimate map 1320, with the larger shift in wavenumber corresponding to the more severe impact. The deviations around the edges in both specimens can be attributed to mishandling of the composite and/or edge effects from the signal processing approach (a phenomenon similar to "leakage" when processing unwindowed one-dimensional signals).

Figure 14:
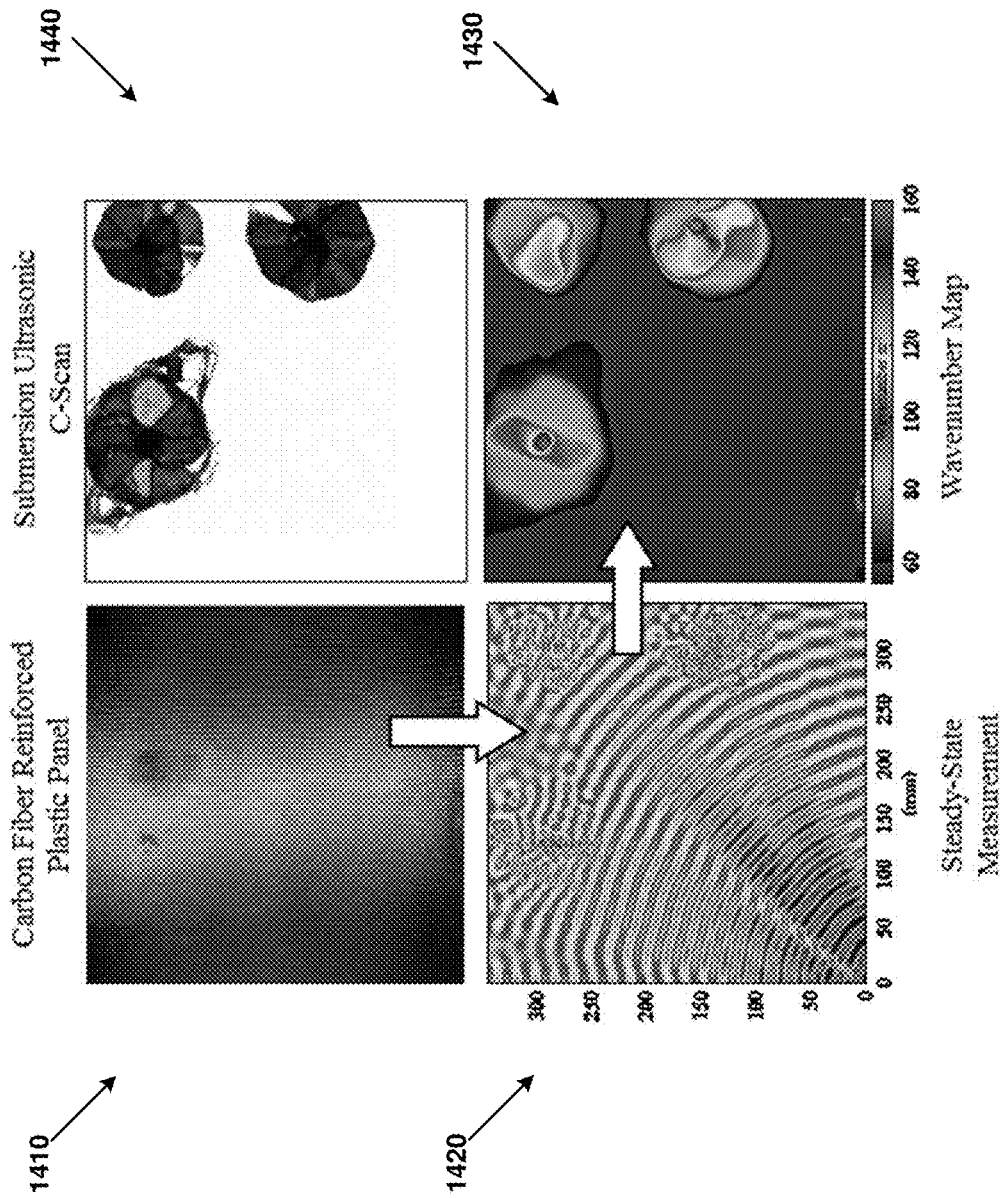

FIG. 14 illustrates results of scanning a carbon fiber reinforced plastic panel, shown in a photograph 1410 using a method disclosed above. The real part of a steady-state measurement is displayed in a chart 1420 and a final wavenumber estimate map 1430 is also displayed. As shown in FIG. 14, the results obtained from steady-state ultrasonic excitation scanning compare favorably to those obtained using another technique, as shown in the chart 1440 of a submersion ultrasonic C-scan.

Having described and illustrated the principles of our innovations in the detailed description and accompanying drawings, it will be recognized that the various embodiments can be modified in arrangement and detail without departing from such principles.

In view of the many possible embodiments to which the principles of the disclosed invention may be applied, it should be recognized that the illustrated embodiments are only preferred examples of the invention and should not be taken as limiting the scope of the invention. We claim as our invention all such embodiments as may come within the scope of the following claims and equivalents thereto.

We claim:

1. A method for analyzing a structure, the method comprising:
   applying a continuous signal having one or more periodic tones to the structure, causing the structure to reach a steady vibration state;
   generating measurements of wave response of the structure to the signal at each of a plurality of inspection points of the structure; and
   for each of the periodic tones, estimating a wavenumber for a number of the inspection points of the structure, by calculating amplitudes of spatial frequency domain data based on the wave response measurements.

2. The method of claim 1, wherein the continuous signal is applied by using a piezoelectric transducer in physical communication with the structure.

3. A method, comprising:
   projecting a laser light onto a surface of a structure, causing the structure to reach a steady vibration state;
   generating measurements of wave response of the structure to the laser light at each of a plurality of inspection points of the structure; and
   estimating a wavenumber for a number of the inspection points of the structure, by calculating amplitudes of spatial frequency domain data based on the wave response measurements.

4. The method of claim 1, wherein the periodic tones have frequencies in a range of 30-500 kHz.

5. A method for analyzing a structure, the method comprising:
   applying a continuous signal having one or more periodic tones to the structure, causing the structure to reach a steady vibration state;
   using a laser Doppler vibrometer, generating measurements of wave response of the structure to the signal at each of a plurality of inspection points of the structure; and
   for each of the periodic tones, estimating a wavenumber for a number of the inspection points of the structure, by calculating amplitudes of spatial frequency domain data based on the wave response measurements.

6. The method of claim 1, wherein the method further comprises identifying a defect in the structure, and wherein the structure comprises a planar metallic or composite material.

7. The method of claim 1, wherein the method further comprises composing the wavenumber into a map of properties of the structure, and wherein the mapped properties include at least one or more of the following: thickness, density, material composition, elasticity, or temperature.

8. The method of claim 1, wherein the wave response measurements are time domain data, and wherein the estimating the wavenumber comprises transforming at least a portion of the wave response measurements into spatial frequency domain data.

9. The method of claim 1, further comprising generating an image or map of at least a portion of the inspection points.

10. The method of claim 1, further comprising:
    determining one or more properties of the structure based on the estimated wavenumber; and
    separating foreground inspection targets from background objects using a mask formed by thresholding vibration responses based on the determined properties.

11. At least one non-transitory computer-readable storage medium storing computer-readable instructions that when executed by a computer, cause the computer to perform the method of claim 1.

12. The method of claim 3, wherein the method further comprises identifying a defect in the structure, and wherein the structure comprises a planar metallic or composite material.

13. The method of claim 3, wherein the method further comprises composing the wavenumber into a map of properties of the structure, and wherein the mapped properties include at least one or more of the following: thickness, density, material composition, elasticity, or temperature.

14. The method of claim 3, wherein the wave response measurements are time domain data, and wherein the estimating the wavenumber comprises transforming at least a portion of the wave response measurements into spatial frequency domain data.

15. The method of claim 3, further comprising generating an image or map of at least a portion of the inspection points.

16. The method of claim 3, further comprising:
    determining one or more properties of the structure based on the estimated wavenumber; and
    separating foreground inspection targets from background objects using a mask formed by thresholding vibration responses based on the determined properties.

17. At least one non-transitory computer-readable storage medium storing computer-readable instructions that when executed by a computer, cause the computer to perform the method of claim 3.

18. The method of claim 5, wherein the periodic tones have frequencies in a range of 30-500 kHz.

19. The method of claim 5, wherein the method further comprises identifying a defect in the structure, and wherein the structure comprises a planar metallic or composite material.

20. The method of claim 5, wherein the method further comprises composing the wavenumber into a map of properties of the structure, and wherein the mapped properties include at least one or more of the following: thickness, density, material composition, elasticity, or temperature.

21. The method of claim 5, wherein the wave response measurements are time domain data, and wherein the estimating the wavenumber comprises transforming at least a portion of the wave response measurements into spatial frequency domain data.

22. The method of claim 5, further comprising generating an image or map of at least a portion of the inspection points.

23. The method of claim 5, further comprising:
    determining one or more properties of the structure based on the estimated wavenumber; and
    separating foreground inspection targets from background objects using a mask formed by thresholding vibration responses based on the determined properties.

24. At least one non-transitory computer-readable storage medium storing computer-readable instructions that when executed by a computer, cause the computer to perform the method of claim 5.

* * * * *